(12) United States Patent
Majlof et al.

(10) Patent No.: US 8,512,538 B2
(45) Date of Patent: Aug. 20, 2013

(54) CAPILLARY ELECTROPHORESIS DEVICE

(75) Inventors: Lars Majlof, Saratoga, CA (US); Ezra Van Gelder, Palo Alto, CA (US)

(73) Assignee: IntegenX Inc., Pleasanton, CA (US)

( * ) Notice: Subject to any disclaimer, the term of this patent is extended or adjusted under 35 U.S.C. 154(b) by 171 days.

(21) Appl. No.: 13/113,968

(22) Filed: May 23, 2011

(65) Prior Publication Data

US 2011/0290648 A1    Dec. 1, 2011

Related U.S. Application Data

(60) Provisional application No. 61/349,680, filed on May 28, 2010.

(51) Int. Cl.
*G05D 23/00* (2006.01)
*G01N 27/447* (2006.01)
*G01N 27/453* (2006.01)

(52) U.S. Cl.
USPC ............ 204/602; 204/451; 236/1 F; 165/288; 219/480; 219/483

(58) Field of Classification Search
USPC ................. 204/450–455, 601–605; 236/1 F; 165/267–269, 287–293; 137/341; 219/476–480, 482–489
See application file for complete search history.

(56) References Cited

U.S. PATENT DOCUMENTS

| | | | |
|---|---|---|---|
| 3,190,310 A | 6/1965 | Honsinger | |
| 3,352,643 A | 11/1967 | Ando et al. | |
| 3,433,257 A | 3/1969 | Jensen | |
| 3,568,692 A | 3/1971 | Metzger et al. | |
| 3,610,274 A | 10/1971 | Levesque et al. | |
| 4,113,665 A | 9/1978 | Law et al. | |
| 4,558,845 A | 12/1985 | Hunkapiller | |
| 4,703,913 A | 11/1987 | Hunkapiller | |
| 4,847,120 A | 7/1989 | Gent | |
| 4,963,498 A | 10/1990 | Hillman et al. | |
| 5,085,757 A | 2/1992 | Karger et al. | |
| 5,275,645 A | 1/1994 | Ternoir et al. | |
| 5,364,759 A | 11/1994 | Caskey et al. | |
| 5,376,252 A | 12/1994 | Ekström et al. | |
| 5,387,505 A | 2/1995 | Wu | |
| 5,453,163 A | 9/1995 | Yan | |
| 5,482,836 A | 1/1996 | Cantor et al. | |
| 5,523,231 A | 6/1996 | Reeve | |
| 5,571,410 A | 11/1996 | Swedberg et al. | |
| 5,587,128 A | 12/1996 | Wilding et al. | |

(Continued)

FOREIGN PATENT DOCUMENTS

| | | | |
|---|---|---|---|
| CA | 2433145 A1 | 5/2002 | |
| EP | 0459241 B1 | 12/1991 | |

(Continued)

OTHER PUBLICATIONS

U.S. Appl. No. 13/202,877, filed Aug. 23, 2011, Vangbo et al.

(Continued)

*Primary Examiner* — J. Christopher Ball

(57) ABSTRACT

This invention provides a capillary electrophoresis device in which capillaries are thermally regulated on a thermally responsive electrical path attached to an electrically insulating circuit board. This invention also provides an optical scanner useful for scanning an array of capillaries. A laser, optical detector and optical selector are in an arrangement that allows the optical detector to selectively detect an optical signal from any one or more of the plurality of electrophoresis capillaries.

35 Claims, 14 Drawing Sheets

(56) References Cited

U.S. PATENT DOCUMENTS

| | | |
|---|---|---|
| 5,635,358 A | 6/1997 | Wilding et al. |
| 5,639,428 A | 6/1997 | Cottingham |
| 5,681,946 A | 10/1997 | Reeve |
| 5,705,628 A | 1/1998 | Hawkins |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,776,748 A | 7/1998 | Singhvi et al. |
| 5,830,662 A | 11/1998 | Soares et al. |
| 5,842,787 A | 12/1998 | Kopf-sill et al. |
| 5,856,174 A | 1/1999 | Lipshutz et al. |
| 5,863,502 A | 1/1999 | Southgate et al. |
| 5,872,010 A | 2/1999 | Karger et al. |
| 5,885,470 A | 3/1999 | Parce et al. |
| 5,898,071 A | 4/1999 | Hawkins |
| 5,900,130 A | 5/1999 | Benvegnu |
| 5,908,552 A | 6/1999 | Zimmerman et al. |
| 5,922,591 A | 7/1999 | Anderson et al. |
| 5,942,443 A | 8/1999 | Parce et al. |
| 5,948,684 A | 9/1999 | Weigl et al. |
| 5,971,158 A | 10/1999 | Yager et al. |
| 5,994,064 A | 11/1999 | Staub et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,110,343 A | 8/2000 | Ramsey et al. |
| 6,120,184 A | 9/2000 | Laurence et al. |
| 6,136,212 A | 10/2000 | Mastrangelo et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,342,142 B1 | 1/2002 | Ramsey |
| 6,348,318 B1 | 2/2002 | Valkirs |
| 6,379,929 B1 | 4/2002 | Burns et al. |
| 6,387,234 B1 | 5/2002 | Yeung et al. |
| 6,387,707 B1 | 5/2002 | Seul et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,191 B2 | 8/2002 | Schutt |
| 6,432,290 B1 | 8/2002 | Harrison et al. |
| 6,454,924 B2 | 9/2002 | Jedrzejewski et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,527,003 B1 | 3/2003 | Webster |
| 6,531,041 B1 | 3/2003 | Cong et al. |
| 6,531,282 B1 | 3/2003 | Dau et al. |
| 6,532,997 B1 | 3/2003 | Bedingham et al. |
| 6,533,914 B1 | 3/2003 | Liu |
| 6,534,262 B1 | 3/2003 | McKernan et al. |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,581,899 B2 | 6/2003 | Williams |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein et al. |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,663,833 B1 | 12/2003 | Stave et al. |
| 6,685,442 B2 | 2/2004 | Chinn et al. |
| 6,685,809 B1 | 2/2004 | Jacobson et al. |
| 6,705,345 B1 | 3/2004 | Bifano |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,063,304 B2 | 6/2006 | Leys |
| 7,087,380 B2 | 8/2006 | Griffiths et al. |
| 7,097,809 B2 | 8/2006 | Van Dam et al. |
| 7,118,910 B2 | 10/2006 | Unger et al. |
| 7,157,228 B2 | 1/2007 | Hashmi et al. |
| 7,169,557 B2 | 1/2007 | Rosenblum et al. |
| 7,198,759 B2 | 4/2007 | Bryning et al. |
| 7,211,388 B2 | 5/2007 | Cash et al |
| 7,232,656 B2 | 6/2007 | Balasubramanian et al. |
| 7,244,961 B2 | 7/2007 | Jovanovich et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,323,305 B2 | 1/2008 | Leamon et al. |
| 7,361,471 B2 | 4/2008 | Gerdes et al. |
| 7,377,483 B2 | 5/2008 | Iwabuchi et al. |
| 7,416,165 B2 | 8/2008 | Ohmi et al. |
| 7,438,856 B2 | 10/2008 | Jedrzejewski et al. |
| 7,445,926 B2 | 11/2008 | Mathies et al. |
| 7,473,342 B2 | 1/2009 | Ugai et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,537,886 B1 | 5/2009 | Nazarenko et al. |
| 7,575,865 B2 | 8/2009 | Leamon et al. |
| 7,645,580 B2 | 1/2010 | Barber et al. |
| 7,691,614 B2 | 4/2010 | Senapathy |
| 7,745,207 B2 | 6/2010 | Jovanovich et al. |
| 7,763,453 B2 | 7/2010 | Clemmens et al. |
| 7,766,033 B2 | 8/2010 | Mathies et al. |
| 7,799,553 B2 | 9/2010 | Mathies et al. |
| 7,803,281 B2 | 9/2010 | Davies |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 | 1/2011 | Nasarabadi |
| 7,885,770 B2 | 2/2011 | Gill et al. |

| Patent/Publication | Date | Inventor |
|---|---|---|
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,972,561 B2 | 7/2011 | Viovy et al. |
| 7,976,789 B2 | 7/2011 | Kenis et al. |
| 7,976,795 B2 | 7/2011 | Zhou et al. |
| 8,007,746 B2 | 8/2011 | Unger et al. |
| 8,018,593 B2 | 9/2011 | Tan et al. |
| 8,037,903 B2 | 10/2011 | Wang et al. |
| 8,053,192 B2 | 11/2011 | Bignell et al. |
| 2001/0041357 A1 | 11/2001 | Fouillet et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2002/0127736 A1 | 9/2002 | Chou et al. |
| 2002/0139084 A1 | 10/2002 | Tobolka |
| 2002/0144738 A1 | 10/2002 | Unger et al. |
| 2002/0148992 A1 | 10/2002 | Hayenga et al. |
| 2002/0157951 A1 | 10/2002 | Foret et al. |
| 2002/0160361 A1 | 10/2002 | Loehrlein et al. |
| 2003/0008308 A1 | 1/2003 | Enzelberger et al. |
| 2003/0021734 A1 | 1/2003 | Vann et al. |
| 2003/0029724 A1 | 2/2003 | Derand et al. |
| 2003/0070677 A1 | 4/2003 | Handique et al. |
| 2003/0077839 A1 | 4/2003 | Takei |
| 2003/0095897 A1 | 5/2003 | Grate et al. |
| 2003/0217923 A1 | 11/2003 | Harrison et al. |
| 2004/0003997 A1 | 1/2004 | Anazawa et al. |
| 2004/0013536 A1 | 1/2004 | Hower et al. |
| 2004/0014091 A1 | 1/2004 | Duck et al. |
| 2004/0018611 A1 | 1/2004 | Ward et al. |
| 2004/0021068 A1 | 2/2004 | Staats |
| 2004/0037739 A1 | 2/2004 | Mcneely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086870 A1 | 5/2004 | Tyvoll et al. |
| 2004/0086872 A1 | 5/2004 | Childers et al. |
| 2004/0132170 A1 | 7/2004 | Storek et al. |
| 2004/0151629 A1 | 8/2004 | Pease et al. |
| 2004/0185484 A1 | 9/2004 | Costa et al. |
| 2004/0197845 A1 | 10/2004 | Hassibi et al. |
| 2004/0200724 A1 | 10/2004 | Fujii et al. |
| 2004/0209354 A1 | 10/2004 | Mathies et al. |
| 2004/0224380 A1 | 11/2004 | Chou et al. |
| 2005/0026300 A1 | 2/2005 | Samper et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0161326 A1 | 7/2005 | Morita et al. |
| 2005/0161669 A1 | 7/2005 | Jovanovich et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0255000 A1 | 11/2005 | Yamamoto et al. |
| 2005/0255003 A1 | 11/2005 | Summersgill et al. |
| 2005/0255007 A1 | 11/2005 | Yamada et al. |
| 2005/0266582 A1 | 12/2005 | Modlin et al. |
| 2005/0287572 A1 | 12/2005 | Mathies et al. |
| 2006/0027456 A1 | 2/2006 | Harrison et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0186043 A1 | 8/2006 | Covey et al. |
| 2006/0260941 A1 | 11/2006 | Tan et al. |
| 2006/0263789 A1 | 11/2006 | Kincaid |
| 2006/0266645 A1 | 11/2006 | Chen et al. |
| 2006/0292032 A1 | 12/2006 | Hataoka et al. |
| 2007/0015179 A1 | 1/2007 | Klapperich et al. |
| 2007/0017812 A1 | 1/2007 | Bousse |
| 2007/0031865 A1 | 2/2007 | Willoughby |
| 2007/0034025 A1 | 2/2007 | Pant et al. |
| 2007/0105163 A1 | 5/2007 | Grate et al. |
| 2007/0113908 A1 | 5/2007 | Lee et al. |
| 2007/0122819 A1 | 5/2007 | Wu et al. |
| 2007/0175756 A1 | 8/2007 | Nguyen et al. |
| 2007/0184463 A1 | 8/2007 | Molho et al. |
| 2007/0202531 A1 | 8/2007 | Grover |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0289941 A1 | 12/2007 | Davies |
| 2007/0297947 A1 | 12/2007 | Sommers et al. |
| 2008/0014576 A1 | 1/2008 | Jovanovich et al. |
| 2008/0014589 A1 | 1/2008 | Link et al. |
| 2008/0047836 A1 | 2/2008 | Strand et al. |
| 2008/0064610 A1 | 3/2008 | Lipovsek et al. |
| 2008/0124723 A1 | 5/2008 | Dale et al. |
| 2008/0138809 A1 | 6/2008 | Kapur et al. |
| 2008/0164155 A1 | 7/2008 | Pease et al. |
| 2008/0179255 A1 | 7/2008 | Jung et al. |
| 2008/0179555 A1 | 7/2008 | Landers et al. |
| 2008/0237146 A1 | 10/2008 | Harrison et al. |
| 2008/0242560 A1 | 10/2008 | Gunderson et al. |
| 2008/0257437 A1 | 10/2008 | Fernandes et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0023603 A1 | 1/2009 | Selden et al. |
| 2009/0035770 A1 | 2/2009 | Mathies et al. |
| 2009/0053799 A1 | 2/2009 | Chang-Yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0092970 A1 | 4/2009 | Williams |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0178934 A1 | 7/2009 | Jarvius et al. |
| 2009/0181411 A1 | 7/2009 | Battrell et al. |
| 2009/0253181 A1 | 10/2009 | Vangbo et al. |
| 2009/0269504 A1 | 10/2009 | Liao |
| 2009/0286327 A1 | 11/2009 | Cho et al. |
| 2009/0311804 A1 | 12/2009 | Mcbrady et al. |
| 2009/0314972 A1 | 12/2009 | Mcavoy et al. |
| 2009/0325277 A1 | 12/2009 | Shigeura et al. |
| 2010/0068723 A1 | 3/2010 | Jovanovich et al. |
| 2010/0111770 A1 | 5/2010 | Hwang et al. |
| 2010/0129810 A1 | 5/2010 | Greiner et al. |
| 2010/0165784 A1 | 7/2010 | Jovanovich et al. |
| 2010/0172898 A1 | 7/2010 | Doyle et al. |
| 2010/0173398 A1 | 7/2010 | Peterman |
| 2010/0197507 A1 | 8/2010 | Rothberg et al. |
| 2010/0210008 A1 | 8/2010 | Strand et al. |
| 2010/0221726 A1 | 9/2010 | Zenhausern et al. |
| 2010/0224255 A1 | 9/2010 | Mathies et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0252123 A1 | 10/2010 | Mathies et al. |
| 2010/0266432 A1 | 10/2010 | Pirk et al. |
| 2010/0285578 A1 | 11/2010 | Selden et al. |
| 2010/0285606 A1 | 11/2010 | Phillips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0326826 A1 | 12/2010 | Harrison et al. |
| 2011/0003301 A1 | 1/2011 | Raymond et al. |
| 2011/0005932 A1 | 1/2011 | Jovanovich et al. |
| 2011/0008813 A1 | 1/2011 | Dilleen et al. |
| 2011/0020920 A1 | 1/2011 | Mathies et al. |
| 2011/0027913 A1 | 2/2011 | Bau et al. |

| | | | |
|---|---|---|---|
| 2011/0038758 A1 | 2/2011 | Akaba et al. | |
| 2011/0039303 A1 | 2/2011 | Jovanovich et al. | |
| 2011/0045505 A1 | 2/2011 | Warthoe et al. | |
| 2011/0048945 A1 | 3/2011 | Harrison et al. | |
| 2011/0053784 A1 | 3/2011 | Unger et al. | |
| 2011/0070578 A1 | 3/2011 | Bell et al. | |
| 2011/0076735 A1 | 3/2011 | Jovanovich et al. | |
| 2011/0124049 A1 | 5/2011 | Li et al. | |
| 2011/0126910 A1 | 6/2011 | May | |
| 2011/0126911 A1 | 6/2011 | Kobrin et al. | |
| 2011/0127222 A1 | 6/2011 | Chang-Yen et al. | |
| 2011/0136179 A1 | 6/2011 | Bin/Lee et al. | |
| 2011/0137018 A1 | 6/2011 | Chang-Yen et al. | |
| 2011/0171086 A1 | 7/2011 | Prins et al. | |
| 2011/0172403 A1 | 7/2011 | Harrold et al. | |
| 2011/0189678 A1 | 8/2011 | Mcbride et al. | |
| 2011/0206576 A1 | 8/2011 | Woudenberg et al. | |
| 2011/0212440 A1 | 9/2011 | Viovy et al. | |
| 2011/0212446 A1 | 9/2011 | Wang et al. | |
| 2011/0223605 A1 | 9/2011 | Bienvenue et al. | |

FOREIGN PATENT DOCUMENTS

| | | |
|---|---|---|
| EP | 0637999 A1 | 2/1995 |
| EP | 0527905 B1 | 11/1995 |
| EP | 1065378 B1 | 4/2002 |
| EP | 1411340 A2 | 4/2004 |
| EP | 1411340 A3 | 5/2004 |
| EP | 1345697 B1 | 6/2007 |
| EP | 1658890 B1 | 5/2008 |
| EP | 1345551 B1 | 4/2009 |
| EP | 2345739 A2 | 7/2011 |
| JP | 2007-506430 A | 7/1995 |
| JP | 408327594 A | 12/1996 |
| JP | 2001-500966 A | 1/2001 |
| JP | 2001-521818 A | 11/2001 |
| JP | 2002-370200 A | 12/2002 |
| JP | 2003-536058 A | 12/2003 |
| JP | 2004-025159 A | 1/2004 |
| JP | 2004-108285 A | 4/2004 |
| JP | 2004-180594 A | 7/2004 |
| JP | 2005-323519 A | 11/2005 |
| JP | 2005-337415 | 12/2005 |
| JP | 2005-345463 A | 12/2005 |
| JP | 2007-155491 A | 6/2007 |
| JP | 2008-513022 A | 5/2008 |
| WO | WO 93/22053 A1 | 4/1993 |
| WO | WO 96/04547 A1 | 2/1996 |
| WO | WO 96/14934 A1 | 5/1996 |
| WO | WO 98/10277 A1 | 7/1997 |
| WO | WO 99/22868 A1 | 10/1998 |
| WO | WO 98/52691 A1 | 11/1998 |
| WO | WO 98/53300 A2 | 11/1998 |
| WO | WO 98/53300 A3 | 2/1999 |
| WO | WO 99/36766 A1 | 7/1999 |
| WO | WO 99/40174 A1 | 8/1999 |
| WO | WO 00/40712 A1 | 7/2000 |
| WO | WO 00/60362 A1 | 10/2000 |
| WO | WO 00/61198 A1 | 10/2000 |
| WO | WO 01/32930 A1 | 5/2001 |
| WO | WO 01/38865 A1 | 5/2001 |
| WO | WO 01/85341 A1 | 11/2001 |
| WO | WO 02/43864 A2 | 11/2001 |
| WO | WO 02/41995 A1 | 5/2002 |
| WO | WO 02/43615 A2 | 6/2002 |
| WO | WO 02/43864 A3 | 8/2002 |
| WO | WO 02/43615 A3 | 3/2003 |
| WO | WO 03/044528 A2 | 5/2003 |
| WO | WO 03/085379 A2 | 10/2003 |
| WO | WO 03/085379 A3 | 12/2003 |
| WO | WO 2004/038363 A2 | 5/2004 |
| WO | WO 03/044528 A3 | 6/2004 |
| WO | WO 2004/061085 A2 | 7/2004 |
| WO | WO 2004/061085 A3 | 10/2004 |
| WO | WO 2004/098757 A2 | 11/2004 |
| WO | WO 2004/038363 A3 | 12/2004 |
| WO | WO 2005/075081 A1 | 8/2005 |
| WO | WO 2005/091820 A2 | 10/2005 |
| WO | WO 2005/108620 A2 | 11/2005 |
| WO | WO 2005/118867 A2 | 12/2005 |
| WO | WO 2005/121308 A1 | 12/2005 |
| WO | WO 2006/032044 A2 | 3/2006 |
| WO | WO 2005/108620 A3 | 4/2006 |
| WO | WO 2004/098757 A3 | 5/2006 |
| WO | WO 2005/091820 A3 | 10/2006 |
| WO | WO 2006/032044 A3 | 1/2007 |
| WO | WO 2007/002579 A2 | 1/2007 |
| WO | WO 2007/064635 A1 | 6/2007 |
| WO | WO 2007/082480 A1 | 7/2007 |
| WO | WO 2007/109375 A2 | 9/2007 |
| WO | WO 2005/118867 A3 | 12/2007 |
| WO | WO 2008/012104 A2 | 1/2008 |
| WO | WO 2008/024319 A2 | 2/2008 |
| WO | WO 2008/024319 A3 | 4/2008 |
| WO | WO 2008/039875 A1 | 4/2008 |
| WO | WO 2008/012104 A3 | 5/2008 |
| WO | WO 2008/115626 A2 | 9/2008 |
| WO | WO 2007/109375 A3 | 10/2008 |
| WO | WO 2008/115626 A3 | 11/2008 |
| WO | WO 2009/008236 A1 | 1/2009 |
| WO | WO 2009/015296 A1 | 1/2009 |
| WO | WO 2007/002579 A3 | 9/2009 |
| WO | WO 2009/108260 A2 | 9/2009 |
| WO | WO 2009/129415 A1 | 10/2009 |
| WO | WO 2009/108260 A3 | 12/2009 |
| WO | WO 2010/041174 A1 | 4/2010 |
| WO | WO 2010/041231 A2 | 4/2010 |
| WO | WO 2010/042784 A2 | 4/2010 |
| WO | WO 2010/042784 A3 | 7/2010 |
| WO | WO 2010/041231 A3 | 9/2010 |
| WO | WO 2010/109392 A1 | 9/2010 |
| WO | WO 2010/130762 A2 | 11/2010 |
| WO | WO 2010/141921 A1 | 12/2010 |
| WO | WO 2011/003941 A1 | 1/2011 |
| WO | WO 2010/130762 A3 | 2/2011 |
| WO | WO 2011/012621 A1 | 2/2011 |
| WO | WO 2011/034621 A2 | 3/2011 |
| WO | WO 2011/084703 A2 | 7/2011 |
| WO | WO 2011/034621 A3 | 11/2011 |

OTHER PUBLICATIONS

U.S. Appl. No. 13/202,884, filed Aug. 23, 2011, Jovanovich et al.
Bennett, et al. Toward the 1,000 dollars human genome. Pharmacogenomics, 6 (4) 373-382. (Jun. 2005).
Chinese office action dated Jan. 31, 2011 for CN 200580035911.7. (In Chinese with English translation).
Erratum for Margulies, et al. Genome sequencing in microfabricated high-density picolitre reactors. Nature. 2005;437(7057):376-80.: Margulies, et al. Nature. 441(7089):120. (May 4, 2006).
International search report dated Sep. 1, 2010 for PCT/US2010/040490.
U.S. Appl. No. 12/026,510, filed Feb. 5, 2008, Jovanovich et al.
U.S. Appl. No. 12/820,390, filed Jun. 22, 2010, Harrison et al.
U.S. Appl. No. 12/845,650, filed Jul. 28, 2010, Jovanovich et al.
U.S. Appl. No. 13/075,165, filed Mar. 29, 2011, Eberhart et al.
Amendment and Request for Correction of Inventorship mailed Jan. 10, 2008 in U.S. Appl. No. 10/750,533.
Anderson, et al. A miniature integrated device for automated multistep genetic assays. Nucleic Acids Research. 2000;28:e60.
Armani, et al. Re-configurable fluid circuits by PDMS elastomer micromachining Proceedings of IEEE Micro Electro Mechanical Systems: MEMS. 1999; 222-227.
Bings, et al. Microfluidic Devices Connected to Fused-Silica Capillaries with Minimal Dead Dead Volume. Analytical Chemistry. 1999;71(15):3292-3296.
Blazej, et al. Microfabricated bioprocessor for integrated nanoliter-scale Sanger DNA sequencing. Proc. Natl. Acad. Sci. USA 2006;103:7240-7245.
Blazej, et al. Polymorphism Ratio Sequencing: A New Approach for Single Nucleotide Polymorphism Discovery and Genotyping. Genome Research. 2003;13:287-293.
Brenner, et al. Gene expression analysis by massively parallel signature sequencing (MPSS) on microbead arrays. Nature Biotechnology. 2000;18(6):630-634.

Buchholz, et al. The use of light scattering for precise characterization of polymers for DNA sequencing by capillary electrophoresis. Electrophoresis. 2001;22:4118-4128.

CAPLUS abstract of Krohkin et al. Modified silica as a stationary phase for ion chromatography. Journal of Chromatography A. 1995;706:93-8.

Chan, et al. Microfabricated Polymer Devices for Automated Sample Delivery of Peptides for Analysis by Electrospray Ionization Tandem Mass Spectrometry. Analytical Chemistry. 1999;71(20):4437-4444.

Chiem, et al. Microchip systems for immunoassay: an integrated immunoreactor with electrophoretic separation for serum theophylline determination. Clinical Chemistry.1998;44(3):591-598.

Chiem, et al. Room temperature bonding of micromachined glass devices for capillary electrophoresis. Sensors and Actuators. 2000;B63(3):147-152.

Coleman, et al. A sequential injection microfluidic mixing strategy. Microfluidics and Nanofluidics. 2005;319-327.

Curcio, et al. Continuous Segmented-Flow Polymerase Chain Reaction for High-Throughput Miniaturized DNA Amplification. Analytical Chemistry. 2003;75(1):1-7.

Datasheet Cycle Sequencing, Retrieved from the internet, URL:http//answers.com/topic/cycle sequencing. Printed Sep. 3, 2010, pp. 1-2.

Diehl, et al. Beaming: single-molecule PCR on microparticles in water-in-oil emulsions. Nature Methods. 2006;3(7):551-9.

Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.

Doherty, et al. Sparsely cross-linked "nanogels" for microchannel DNA sequencing. Electrophoresis. 2003;24(24):4170-4180.

Dorfman, et al. Contamination-Free Continuous Flow Microfluidic Polymerase Chain Reaction for Quantitative and Clinical Applications. Analytical Chemistry. 2005;77(11):3700-3704.

Doyle, et al. Self-Assembled Magnetic Matrices for DNA Separation Chips. Science. 2000;295:2237.

Dressman, et al. Transforming single DNA molecules into fluorescent magnetic particles for detection and enumeration of genetic variations. Proc Natl Acad Sci USA. 2003;100(15):8817-8822.

Emrich, et al. Microfabricated 384-Lane Capillary Array Electrophoresis Bioanalyzer for Ultrahigh-Throughput Genetic Analysis. Analytical Chemistry. 2002;74(19):5076-5083.

Ericson, et al. Electroosmosis- and Pressure-Driven. Chromatography in Chips Using Continuous Beds. Analytical Chemistry. 2000;72(1):81-87.

European search report and search opinion dated Jun. 6, 2011 for Application No. 10011511.2.

European search report dated Dec. 18, 2009 for Application No. 03808583.3.

European search report dated Sep. 1, 2010 for Application No. 5804847.1.

Ewing, et al. Base-Calling of Automated Sequencer Traces Using Phred. I. Accuracy Assessment. Genome Research. 1998;8:175-185.

Ewing, et al. Base-Calling of Automated Sequencer Traces Using Phred. II. Error probabilities. Genome Research. 1998;8:186-194.

Figeys, et al. A Microfabricated Device for Rapid Protein Identification by Microelectrospray Ion Trap Mass Spectrometry. Analytical Chemistry. 1997;69(16):3153-3160.

Figeys, et al. An Integrated Microfluidics-Tandem Mass Spectrometry System for Automated Protein Analysis. Analytical Chemistry. 1998;70(18):3728-3734.

Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.

Figeys, et al. Nanoflow Solvent Gradient Delivery from a Microfabricated Device for Protein Identifications by Electrospray Ionization Mass Spectrometry. Analytical Chemistry. 1998;70(18):3721-3727.

Francis, et al. Flow analysis based on a pulsed flow of solution: theory, instrumentation and applications. Talanta. 2002;58(6):1029-1042.

Ghadessy, et al. Directed evolution of polymerase function by compartmentalized self-replication. Proc Natl Acad Sci USA. 2001;98:4552-4557.

Giddings, et al. A software system for data analysis in automated DNA sequencing. Genome Research. 1998;644-665.

Goll, et al. Microvalves with bistable buckled polymer diaphragms. Journal of Micromechanics and Microengineering. 1996;6:77-79.

Grover, et al. An integrated microfluidic processor for single nucleotide polymorphism-based DNA computing. Lab on a Chip. 2005;5(10):1033-1040.

Grover, et al. Development and multiplexed control of latching pneumatic valves using microfluidic logical structures. Lab on a chip. 2006;6:623-631.

Grover, et al. Monolithic membrane valves and diaphragm pumps for practical large-scale integration into glass microfluidic devices. Sensors and Actuators. 2003;B89:315-323.

Grover, et al. Practical Valves and Pumps for Large-Scale Integration into Microfludic Analysis Devices. Micro Total Analysis Systems. 2002;1:136-138.

Hansen, et al. A robust and scalable microfluidic metering method that allows protein crystal growth by free interface diffusion. Proc Natl Acad Sci USA. 2002 ;99(26):16531-16536.

Harrison, et al. Micromachining a Miniaturized Capillary Electrophoresis-Based Chemical Analysis System on a Chip. Science. 1993;261(5123):895-897.

Hayes, et al. EDGE: A Centralized Resource for the Comparison, Analysis, and Distribution of Toxicogenomic Information. Molecular Pharmacology. 2005;67(4):1360-1368.

Hultman, et al. Bidirectional Solid-Phase Sequencing of in Vitro-Amplified Plasmid DNA. BioTechniques. 1991;10(1):84-93.

International Preliminary Report for corresponding PCT Application No. PCT/CA2000/01421 dated Feb. 14, 2002.

International Preliminary Report for corresponding PCT Application No. PCT/US2005/018678 dated Nov. 13, 2007.

International Preliminary Report for corresponding PCT Application No. PCT/US2005/033347 dated Mar. 20, 2007.

International Preliminary Report for corresponding PCT Application No. PCT/US2007/007381 dated Sep. 23, 2008.

International Preliminary Report for corresponding PCT Application No. PCT/US2007/02721 dated Aug. 5, 2008.

International Preliminary Report for corresponding PCT Application No. PCT/US2007/061573 dated Aug. 26, 2008.

International search report and written opinion dated Mar. 24, 2011 for PCT Application No. US2010/58227.

International search report and written opinion dated Jun. 9, 2011 for PCT Application No. US2011/30973.

International search report and written opinion dated Sep. 1, 2010 for PCT Application No. US2010/040490.

International search report dated Oct. 6, 2010 for PCT Application No. US10/37545.

International search report dated Apr. 5, 2001 for PCT Application No. CA2000/01421.

International search report dated May 14, 2010 for PCT Application No. US2009/06640.

International search report dated Jul. 11, 2008 for PCT Application No. US07/61573.

International search report dated Jul. 30, 2010 for PCT Application No. US2010/36464.

International search report dated Aug. 18, 2009 for PCT Application No. US09/00419.

International search report dated Aug. 23, 2006 for PCT Application No. US2005/033347.

International search report dated Aug. 26, 2004 PCT Application No. US2003/41466.

International search report dated Sep. 25, 2007 for PCT Application No. US2007/02721.

International Search Report for PCT/US2005/033347.

Jacobson, et al. Electrokinetic Focusing in Microfabricated Channel Structures. Anal. Chem., 1997, 69 (16), pp. 3212-3217.

Japanese Office Action dated Dec. 21, 2010 for Application No. JP2001-540363 (in Japanese with English translation).

Japanese Office Action dated Apr. 27, 2010 for Application No. JP2001-540363 (in Japanese with English translation).

Ju, et al. Fluorescence energy transfer dye-labeled primers for DNA sequencing and analysis. Proc. Natl. Acad. Sci. USA. 1995;92:4347-4351.

Kan, et al. A novel thermogelling matrix for microchannel DNA sequencing based on poly-N-alkoxyalkylaclylamide copolymers. Electrophoresis. 2003;24(24):4161-4169.

Koh, et al. Integrating Polymerase Chain Reaction, Valving, and Electrophoresis in a Plastic Device for Bacterial Detection. Analytical Chemistry. 2003;75(17):4591-4598.

Kopp, et al. Chemical Amplification Continuous-Flow PCR on a Chip. Science. 1998;280:1046-1048.

Lagally, et al. Fully integrated PCR-capillary electrophoresis microsystem for DNA analysis. Lab on a Chip. 2001;1(2):102-107.

Lagally, et al. Integrated Portable Genetic Analysis Microsystem for Pathogen/Infectious Disease Detection. Analytical Chemistry. 2004;76:3162-3170.

Lagally, et al. Monolithic integrated microfluidic DNA amplification and capillary electrophoresis analysis system. Sensors and Actuators. 2000;B63(3):138-146.

Lagally, et al. Single-Molecule DNA Amplification and Analysis in an Integrated Microfluidic Device. Analytical Chemistry. 2001;73(3): 565-570.

Lazar, et al. Subattomole-Sensitivity Microchip Nanoelectrospray Source with Time-of-Flight Mass Spectrometry Detection. Analytical Chemistry. 1999;71(17):3627-3631.

Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.

Li, et al. Rapid and sensitive separation of trace level protein digests using microfabricated devices coupled to a quadrupole—time-of-flight mass spectrometer. Electrophoresis. 2000;21:198-210.

Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.

Licklider, et al. A Micromachined Chip-Based Electrospray Source for Mass Spectrometry. Analytical Chemistry. 2000;72(2):367-375.

Lisec, et al. A bistable pneumatic microswitch for driving fluidic components. Sensors and Actuators. 1996;A54:746-749.

Liu, et al. Automated parallel DNA sequencing on multiple channel microchips. Proc. Natl. Acad. Sci. USA. 2000;97(10):5369-5374.

Liu, et al. Optimization of High-Speed DNA Sequencing on Microfabricated Capillary Electrophoresis Channels. Analytical Chemistry. 1999;71:566-573.

Margulies, et al. Genome sequencing in microfabricated high-density picolitre reactors. Nature. 2005;437(7057):376-80. (Abstact only).

Melin, et al. A Passive 2-Dimensional Liquid Sample Micromixer. 7th International Conference on Miniaturized Chemical and Biochemical Analysis Systems. 2003;167-170.

MillGat pump user manual, version 2.12, published 2005, pp. 1-28.

Mitra, et al. Digital genotyping and haplotyping with polymerase colonies. Proc Natl Acad Sci USA. 2003.100(10):15926-5931.

Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.

Notice of allowance dated Jun. 9, 2011 for U.S. Appl. No. 12/831,949.

Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.

Ocvirk, et al. High Performance Liquid Chromatography Partially Integrated onto a Silicon Chip. Analytical Methods and Instrumentation. 1995;2:74-82.

Ocvirk, et al. Optimization of confocal epifluorescence microscopy for microchip-based miniaturized total analysis systems. The Analyst. 1998;123:1429-1434.

Office Action Final dated Feb. 19, 2008 issued in U.S. Appl. No. 10/540,658.

Office Action Final dated Feb. 6, 2008 issued in U.S. Appl. No. 11/139,018.

Office Action mailed Apr. 27, 2007 in U.S. Appl. No. 11/139,018, filed May 25, 2005.

Office Action mailed Jul. 2, 2007 in U.S. Appl. No. 10/540,658, filed Jun. 23, 2005.

Office Action mailed Jul. 12, 2007 in U.S. Appl. No. 10/750,533, filed Dec. 29, 2003.

Ohori, et al. Partly disposable three-way mirovalve for a medical micro total analysis system (muTAS). Sensors and Actuators. 1998;A64(1): 57-62.

Oleschuk, et al. Trapping of Bead-Based Reagents within Microfluidic Systems: On-Chip Solid-Phase Extraction and Electrochromatography. Analytical Chemistry. 2000;72:585-590.

Olsen, et al. Immobilization of DNA Hydrogel Plugs in Microfluidic Channels. Analytical Chemistry. 2002;74:1436-1441.

Paegel, et al. High-throughput DNA sequencing with a 96-lane capillary array electrophoresis bioprocessor. Proc Natl Acad Sci USA. 2002;99:574-579.

Paegel, et al. Microchip Bioprocessor for Integrated Nanovolume Sample Purification and DNA Sequencing. Analytical Chemistry. 2002;74(19):5092-5098.

Paegel, et al. Microfluidic devices for DNA sequehcing: sample preparation and electrophoretic analysis. Current Opinion in Biotechnology. 2003;14(1):42-50.

Paegel, et al. Turn Geometry for Minimizing Band Broadening in Microfabricated Capillary Electrophoresis Channels. Analytical Chemistry. 2000;72:3030-3037.

PCT Notification of Transmittal of the International Search Report and the Written Opinion of the International Searching Authority, or the Declaration, mailed Jun. 17, 2008, Application No. PCT/US2007/082568.

Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.

Ramsey, et al. Generating Electrospray from Microchip Devices Using Electroosmotic Pumping. Analytical Chemistry. 1997;69(6):1174-1178.

Rohr, et al. Porous polymer monoliths: Simple and efficient mixers prepared by direct polymerization in the channels of microfluidic chips. Electrophoresis. 2001;22:3959-3967.

Rye, et al. High-sensitivity two-color detection of double-stranded DNA with a confocal fluorescence gel scanner using ethidium homodimer and thiazole orange. Nucleic Acids Research. 1991;19(2):327-333.

Scherer, et al. High-Pressure Gel Loader for Capillary Array Electrophoresis Microchannel Plates. Biotechniques. 2001;31(5):1150-1154.

Schomburg, et al. Design Optimization of Bistable Microdiaphragm Valves. Sensors and Actuators. 1998;A64:259-264.

Seifar, et al. Capillary electrochromatography with 1.8-mum ODS-modified porous silica particles. Journal of Chromatography. 1998; A808:71-77.

Simpson, et al. High-throughput genetic analysis using microfabricated 96-sample capillary array electrophoresis microplates. Proc Natl Acad Sci USA. 1998;95:2256-2261.

Simpson, et al. Microfabrication Technology for the Production of Capillary Array Electrophoresis Chips. Biomedical Microdevices. 1998;1:7-26.

Soper, et al. Sanger DNA Sequencing Reactions Performed in a Solid-Phase Nanoreactor Directly Coupled to Capillary Gel Electrophoresis. Analytical Chemistry. 1998;70:4036-4043.

Spiering, et al. Novel microstructures and technologies applied in chemical analysis techniques. 1997 International Conference on Solid-State Sensors and Actuators. 1997;1:511-514.

Takao, et al. A Pneumatically Actuated Full In-Channel Microvalve With MOSFET-Like Function in Fluid Channel Networks. Journal of Microelectromechanical Systems. 2002;11(5):421-426.

Takao, et al. Microfluidic Integrated Circuits for Signal Processing Using Analogous Relationship Betweeen Pneumatic Microvalve and MOSFET. Journal of Microelectromechanical Systems. 2003;12(4):497-505.

Thomas, et al. Application of Genomics to Toxicology Research. Environmental Health Perspectives. 2002;110(6):919-923.

Thorsen, et al. Microfluidic Large-Scale Integration. Science. 2002;298(5593):580-584.

Tice, et al. Formation of Droplets and Mixing in Multiphase Microfluidics at Low Values of the Reynolds and the Capillary Numbers. Langmuir. 2003;19:9127-9133.

Unger, et al. Monolithic Microfabricated Valves and Pumps by Multilayer Soft Lithography. Science. 2000;288:113-116.

Van Der Moolen, et al. A Micromachined Injection Device for CZE: Application to Correlation CZE. Analytical Chemistry. 1997;69(20):4220-4225.

Van Der Moolen, et al. Correlation Capillary Zone Electrophoresis, a Novel Technique to Decrease Detection Limits. Chromatographia. 1995;40(7/8):368-374.

Vazquez, et al. Electrophoretic Injection within Microdevices. Analytical Chemistry. 2002;74:1952-1961.

Veenstra, et al. The design of an in-plane compliance structure for microfluidical systems. Sensors and Actuators. 2002;B81:377-383.

Waller, et al. Quantitative Immunocapture PCR Assay for Detection of Campylobacter jejuni in Foods. Applied Environmental Microbiology. 2000; 66(9):4115-4118.

Weimer, et al. Solid-Phase Capture of Proteins, Spores, and Bacteria. Applied Environmental Microbiology. 2001;67(3):1300-1307.

Wen, et al. Microfabricated isoelectric focusing device for direct electrospray ionization-mass spectrometry. Electrophoresis. 2000;21:191-197.

Wikipedia brochure for defining stocahstic process. Sep. 2, 2009.

Williams, et al. Amplification of complex gene libraries by emulsion PCR. Nature Methods. 2006;3(7):545-50.

Woolley, et al. Functional Integration of PCR Amplification and Capillary Electrophoresis in a Microfabricated DNA Analysis Device. Analytical Chemistry. 1996;68(23):4081-4086.

Wright, et al. Behavior and Use of Nonaqueous Media without Supporting Electrolyte in Capillary Electrophoresis and Capillary Electrochromatography. Analytical Chemistry. 1997;69(16):3251-3259.

Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.

Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.

Xue, et al. Multichannel Microchip Electrospray Mass Spectrometry. Analytical Chemistry. 1997;69(3):426-430.

Yang, et al. A MEMS thermopneumatic silicone rubber membrane valve. Sensors and Actuators. 1998;A64(1):101-108.

Yu, et al. Preparation of Monolithic Polymers with Controlled Porous Properties for Microfluidic Chip Applications Using Photoinitiated Free Radial Polymerization. Journal of Polymer Science. 2002;40:755-769.

Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.

Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.

Zhang, et al. Microfabricated Devices for Capillary Electrophoresis-Electrospray Mass Spectrometry. Analytical Chemistry. 1999;71(15):3258-3264.

U.S. Appl. No. 13/287,398, filed Nov. 2, 2011, Jovanovich et al.

Chinese office action dated Jul. 8, 2011 for CN 200580035911.7. (In Chinese with English translation).

International search report and written opinion dated Jan. 5, 2012 for PCT Application No. US2011/048527.

International search report and written opinion dated Oct. 26, 2011 for PCT Application No. US11/38180.

International written opinion dated Oct. 6, 2010 for PCT Application No. US10/37545.

International written opinion report dated Jul. 30, 2010 for PCT Application No. US2010/36464.

Japanese office action dated May 27, 2011 for Application No. 2007-532553 (in Japanese with English translation).

Japanese office action dated Jul. 28, 2011 for Application No. 2008-553535 (in Japanese with English translation).

Bianco, et al. Teflon-like coatings for micro devices. CPAC Satellite Workshops. Rome, Italy. Mar. 23, 2009.

Blaga, et al. Microfluidic device for automated sample preparation. Poster. MSB Conference. Dalian, China. Oct. 2009.

Blaga, et al. Plastic chips with valves and pumps. MSB Conference. Berlin, Germany. Mar. 2008. Abstract only.

Franklin, et al. Apollo 200: an integrated platform for DNA profiling. Poster. MCB Conference. Prague, Czech Republic. Mar. 2010.

International search report and written opinion dated Apr. 30, 2012 for PCT/US2012/021217.

Japanese office action dated May 11, 2012 for Application No. 2008-553535 (English translation).

Lee, et al. Polymer nanoengineering for biomedical applications. Annals Biomed. Eng. 2006; 34:75-88.

Lu, et al. New valve and bonding designs for microfluidic biochips containing proteins. Anal. Chem. 2007; 79:994-1001.

Office action dated May 22, 2012 for U.S. Appl. No. 12/526,015.

Oh, et al. A review of microvalves. J. Micromech. Microeng. 2006; 16:R13-R39.

Samel. Novel Microfluidic devices based on a thermally responsive PDMS composite. KTH Royal Institute of Technology, Stockholm, Sweden. 2007; 1-80.

Tajima, et al. Physiochemical properties and morphology of fluorocarbon films synthesized on crosslinked polyethylene by capacitively coupled octafluorocyclobutane plasma. J. Phys. Chem. C. 2007; 111(11):4358-4367.

Willis, et al. Monolithic teflon membrane valves and pumps for harsh chemical and low-temperature use. Lab Chip. 2007; 7:1469-1474.

Zhang, et al. PMMA/PDMS valves and pumps for disposable microfluidics. Lap Chip. 2009; 9:3088-3094.

Allowed Claims dated May 6, 2010 for U.S. Appl. No. 11/726,701.

Allowed Claims dated Jul. 1, 2010 for U.S. Appl. No. 11/139,018.

Allowed Claims dated Aug. 13, 2008 for U.S. Appl. No. 10/750,533.

Auroux, et al.Micro Total Analysis Systems 2. Analytical Standard Operations and Applications. Anal. Chem. 2002; 2637-2652.

Belgrader, et al. A Minisonicator to Rapidly Disrupt Bacterial Spores for DNA Analysis. Anal. Che. 1999; 4232-4236.

Belgrader, et al. PCR Detection of Bacteria in Seven Minutes. Science Magazin. 1999; 284(5413):449-450.

Belgrader, et al.Rapid PCR for Identity Testing Using a Battery-Powered Miniature Thermal Cycler. J Forensic Sci. 1998; 315-319.

Birnboim. A Rapid Alkaline Extraction Method for the Isolation of Plasmid DNA. Methods of Enzymology. 1983; 100:243-255.

Blazej, et al. Inline injection microdevice for attomole-scale sanger DNA sequencing. Anal Chem. Jun. 15, 2007;79(12):4499-506. Epub May 12, 2007.

Burns, et al. An Integrated Nanoliter DBA Analysis Device. Science Magazine. 1998; 484-487.

Call, et al. Detecting and genotyping *Escherichia coli* 0157:H7 using multiplexed PCR and nucleic acid microarrays. International Journal of Food Microbiology. 2001; 67:71-80.

Cameron, et al. High Internal Phase Emulsions (HIPEs) Structure, Properties and Use in Polymer Preparation. University of Strathclyde. 1995; 163214.

Canadian Office Action dated Jun. 10, 2011 for CA Application No. 2512071.

Capanu, et al. Design Fabrication and Testing of a Bistable Electromagnetically Actuated Microvalve. Journal of Microelectromechanical System. 2000; 9:181-189.

Chandler, et al. Automated immunomagnetic separation and microarray detection of *E. coli* 0157:H7 from poultry carcass rinse. International Journal of Food Microbiology. 2001; 70:143-154.

Charlieu, et al. 3' Alu PCR: a simple and rapid method to isolate human polymorphic markers. Nucleic Acids Res. Mar. 25, 1992;20(6):1333-7.

Chinese Office Action dated Jan. 25, 2008 for Application No. 2003801100666.

Chinese office action dated Feb. 24, 2010 for CN Application No. 200780018073.1.

Delehanty, et al. A Microarray Immunoassay for Simultaneous Detection of Proteins and Bacteria. Anal. Chem. 2002; 74:5681-5687.

Dodson, et al. Fluidics Cube for Biosensor Miniaturization. Anal. Chem. 2001; 3776-3780.

Duffy, et al. Rapid Prototyping of Microfluidic Systems in Poly(dimethylsiloxane). Anal. Chem. 1998; 4974-4984.

European office action dated Apr. 7, 2011 for EP Application No. 05804847.1.

Gau, et al. A MEMS based amperometric detector for *E. coli* bacteria using self-assembled monolayers. Biosensors & Bioelectronic. 2001; 16:745755.

Hansen, et al. Polymerase chain reaction assay for the detection of *Bacillus cereus* group cells. FEMS Microbology Letters. 2001; 202:209-213.

Hartmann, et al. Direct immobilization of antibodies on phthalocyaninato-polysiloxane photopolymers. Thin Solid Films. 1994; 245:206-210.

Hartmann, et al. One-step immobilization of immunoglobulin G and potential of the method for application in immunosensors. Sensors and Actuators. 1995; 28 (2):143-149.

He, et al. Fabrication of Nanocolumns for Liquid Chromatography. Anal. Chem. 1998; 3790-3797.

Hjerten. High-performance electrophoresis : Elimination of electroendosmosis and solute adsorption. J. Chromotography. 1985; 347:191-198.

Hosokawa, et al. A Pneumatically-Actuated Three-Way Microvalve Fabricated with Polydimcthylsiloxanc Using the Membrane Transfer Technique. J. Micinicch. Microcng. 2000; 10:415-420.

International search report and written opinion dated Oct. 29, 2007 for PCT/US2005/018678.

International search report and written opinion dated Mar. 16, 2012 for PCT/US2011/048528.

International search report and written opinion dated Jul. 15, 2008 for PCT/US2007/007381.

Jacobson, et al. High-Speed Separations on a Microchip. Anal. Chem. 1994; 1114-1118.

Jacobson, et al. Integrated Microdevice for DNA Restriction Fragment Analysis Anal. Chem. 1996; 720-723.

Japanese Office Action dated Jan. 13, 2010 for JP Application No. 2005508628.

Japanese office action dated Mar. 1, 2011 for JP Application. No. 2007-515379.

Japanese Office Action dated Aug. 10, 2010 for JP Application No. 2005508628.

Kamei, et al. Integrated Amorphous Silicon Photodiode Detector for Microfabricaqted Capillary Electrophoresis Devices. Micro Total Analysis Systems. 2002; 257-259.

Kamei, et al. Integrated hydrogenated amorphous Si photodiode detector for microfluidic bioanalytical devices. Anal Chem. Oct. 15, 2003;75(20):5300-5.

Kimura, et al. Restriction-Site-Specific PCR as a Rapid Test to Detect Enterohemorrhagic *Escherichia coli* O157:H7 Strains in Environmental Samples. Applied and Environmental Microbiology. Jun. 2000; 25132519.

Koch, et al. Optical flow-cell multichannel immunosensor for the detection of biological warfare agents. Biosens Bioelectron. Jan. 2000;14(10-11):779-84.

Kong, et al. Rapid detection of six types of bacterial pathogens in marine waters by multiplex PCR. Water Research. 2002; 36: 2802-2812.

Kourentzi, et al. Microbial identification by immunohybridization assay of artificial RNA labels. Journal of Microbiological Methods. 2002; 49:301-306.

Kuhnert, et al. Detection System for *Escherichia coli*-Specific Virulence Genes: Absence of Virulence Determinants in B and C Strains. applied and Environmental Microbiology. 1997:703-709.

Ligler, et al. Integrating Waveguide Biosensor. Anal Chem. Feb. 1, 2002;74(3):713-9.

Manz, et al. Miniaturized Total Chemical Analysis Systems: A Novel Concept for Chemical Sensing. Sensors & Actuators. 1990; 244-248.

McLaughlin, et al. Molecular Approaches to the Identification of Streptococci. Methods in Molecular Medicine. 1998; 15:117-139.

Medintz, et al. Genotyping Energy-Transfer Cassette Labeled Short Tandem Repeat Amplicons with Capillary Array Electrophoresis Microchannel Plates. Clinical Chemistry. 2001; 1614-1621.

Medintz, et al. High-Performance Genetic Analysis Using Microfabricated Capillary Array Electroporesis Microplates. Electrophoresis. 2001; 38453856.

Medintz, et al. High-Performance Multiplex SNP Analysis of Three Hemochmroinatosis-Related Mutations with Capillary Array Electrophoresis Microplates. Genome Research. 2001; 413-421.

Medintz, et al. Novel Energy Transfer Fluorescence Labeling Cassette. BioTechniques. 2002; 32(2):270.

Nataro, et al. Diarrheagenic *Escherichia coli*. Clinical MicroBiology Reviews. Jan. 1998;142-201.

Notice of Allowance dated May 6, 2010 for U.S. Appl. No. 11/726,701.

Notice of Allowance dated Jul. 1, 2010 for U.S. Appl. No. 11/139,018.

Notice of Allowance dated Aug. 13, 2008 for U.S. Appl. No. 10/750,533.

Office action dated Jan. 7, 2011 for U.S. Appl. No. 12/844,544.
Office action dated Jan. 20, 2010 for U.S. Appl. No. 11/978,224.
Office action dated Feb. 22, 2010 for U.S. Appl. No. 11/139,018.
Office action dated Mar. 2, 2008 for U.S. Appl. No. 10/540,658.
Office action dated Mar. 29, 2012 for U.S. Appl. No. 12/789,186.
Office action dated Mar. 30, 2012 for U.S. Appl. No. 12/795,515.
Office action dated Apr. 11, 2012 for U.S. Appl. No. 11/139,018.
Office action dated Apr. 29, 2009 for U.S. Appl. No. 11/139,018.
Office action dated Aug. 27, 2008 for U.S. Appl. No. 11/139,018.
Office action dated Oct. 8, 2008 for U.S. Appl. No. 10/540,658.
Office action dated Oct. 25, 2010 for U.S. Appl. No. 11/978,224.
Office action dated Nov. 6, 2009 for U.S. Appl. No. 11/139,018.
Office action dated Dec. 11, 2009 for U.S. Appl. No. 11/726,701.

O'Mahony, et al. A real time PCR assay for the detection and quantitation of *Mycobacterium avium* subsp. Paratuberculosis using SYBR Green and the Light Cycler. Journal of Microbiological Methods. 2002; 51:283-293.

Papadelli, et al. Rapid detection and identification of *Streptococcus macedonicus* by species-specific PCR and DNA hybridisation. International Journal of Food Microbiology. 2003; 81:231-239.

Peng, et al. Immuno-capture PCR for detection of *Aeromonas hydrophila* Journal of Microbiological Methods. 2002; 49:335-338.

Press, et al., An Integrated Microfluidic Processor for Single Nucleotide Polymorphism-based DNA Computing, Lab on a Chip. 2005, 5:10, 8 pages.

Press, et al., The Art of Scientific Computing, Numerical Recipes in C, 2nd Edition, Cambridge University Press, 1992, (table of Contents).

Quake, et al. From Micro-to Nanofabrication with Soft Materials. Science Magazine. 2000; 1536-1540.

Reyes, et al. Micro Total Analysis Systems. 1. Introduction Theory and Technology. Anal Chem. 2002; 2623-2636.

Roth, et al. Fundamentals of Logic Design, $3^{rd}$ Edition, West Publishing Company, 1985 (Table of Content).

Rowe, et al. Array Biosensor for Simultaneous Identification of Bacterial, Viral and Protein Analytes. Anal. Chem. 1999; 71:3846-3852.

Rowe-Taitt, et al., Simultaneous detection of six biohazardous agents using a planar waveguide array biosensor. Biosensors & Bioelectronics. 2000; 15:579-589.

Ruan, et al. Immunobiosensor Chips for Detection of *Escherichia coli* O157:H7 Using Electrochemical Impedance Spectroscopy. Anal. Chem. 2002; 74:4814-4820.

Sanford, et al. Photoactivatable Cross-Linked Polyacrylamide for the Site-Selective Immobilization of Antigens and Antibodies Chem Mater. 1998; 10(6): 15101520.

Shi, et al. Radial Capillary Array Electrophoresis Microplate and Scanner for High Performance Nucleic Acid Analysis. Anal. Chem. 1999; 5354-5361.

Soper, et al. Polymeric Microelectro-mechanical Systems. Anal. Chem 2000; 643-651.

Stumpfle, et al. Absence of DNA sequence homology with genes of the *Excherichia coli* hemB locus in Shiga-toxin producing *E. coli* (STEC) 0157 Strains. FEMS Microbiology Letters. 1999; 174:97-103.

Sun, et al. A Heater-Integrated Transparent Microchannel Chip for Continuous Flow PCR. Sensors and Actuators B. 2002; 84:283-289.

Tian, et al. Evaluation of Silica Resins for Direct and Efficient Extraction of DNA from Complex Biological Matrices in a Miniaturized Format. Analytical Biochemistry. 2000; 283:175-191.

Verlee, et al. .Fluid Circuit Technology: Integrated Interconnect Technology for Miniature Fluidic Devices. Abbott Laboratories Hospital Division, Abbott Park, IL. 1996; 9-14.

Walt, et al. Biological Warefare Detection. Analytical Chemistry 2000; 739-746.

Waters, et al. Microchip Device for Cell Lysis, Multiplex PCR Amplification, and Electrophoretic Sizing. Anal. Chem. 1999; 158-162.

Webster, et al. Monolithic Capillary Electrophoresis Device with Integrated Flurorescence Detector. Anal. Chem. 2001;1622-1626.

White, et al. Flash detection/identification of pathogens, bacterial spores and bioterrorism agent biomarker from clinical and environmental matrices. Journal of Microbiological Methods. 2002; 48:139-147.

Yacoub-George, et al. Chemiluminescence multichannel immunosensor for biodetection Analytica Chimica Acta. 2002; 457:3-12.

Yang, et al. An Integrated Stacked Microlaboratory for Biological Agent Detection with DNA and Immunoassays. Biosensors & Bioelectronics. 2002; 17:605-618.

Zhu, et al. High-Sensitivity Capillary Electrophoresis of Double-Stranded DNA Fragments Using Monomeric and Dimeric Fluorescent Intercalating Dyes. Anal Chem. 1994; 1941-1948.

U.S. Appl. No. 13/349,832, filed Jan. 13, 2012, Eberhart et al.

U.S. Appl. No. 13/367,326, filed Feb. 6, 2012, Jovanovich et al.

U.S. Appl. No. 13/384,753, filed Jan. 18, 2012, Stern et al.

Chinese office action dated Jan. 18, 2012 for CN 200980108368.7. (In Chinese with English translation).

Japanese office action dated Jan. 5, 2012 for Application No. 2007-532553 (in Japanese with English translation).

U.S. Appl. No. 90/011,453, filed Jan. 21, 2011, Mathias et al.

European search report and search opinion dated Aug. 17, 2011 for Application No. 08799648.4.

Notice of allowance dated Sep. 8, 2011 for U.S. Appl. No. 12/820,390.

CAPILLARY ELECTROPHORESIS DEVICE

CROSS-REFERENCE

This application claims the benefit of the filing date of corresponding provisional patent application 61/349,680, filed May 28, 2010, the contents of which are incorporated by reference in their entirety.

STATEMENT AS TO FEDERALLY SPONSORED RESEARCH

This invention was made with government support under Contract No. 2004*H838109*000 awarded by the Central Intelligence Agency. The government has certain rights in the invention.

BACKGROUND OF THE INVENTION

Capillary electrophoresis is used in biochemical analysis to detect analytes in a mixture. One popular application is analysis of nucleic acids that are the product of sequencing or amplification reactions. Modern capillary electrophoresis devices use arrays of capillaries to perform multiplex analysis. Such devices regulate temperature in the capillaries in a variety of ways. One method circulates air at a particular temperature around the capillaries, such as in U.S. Pat. No. 7,601,252. In another method the capillaries are in thermal contact with a heating plate, such as in U.S. Pat. Nos. 7,223,326 and 7,473,342.

Analytes in capillary arrays are detected using a variety of optical assemblies.

SUMMARY OF THE INVENTION

Thermal Apparatus

One aspect of the technology is an apparatus with an electrically insulating circuit board, at least one electrical path attached to the circuit board, and at least one electrophoresis capillary in thermal contact with at least one thermal area. The electrical path forms a thermal area. The electrical path is thermally regulated responsive to electrical current through the electrical path. The at least one electrophoresis capillary is thermally regulated responsive to electrical current through the electrical path.

One embodiment includes at least one temperature sensor in thermal contact with the electrophoresis capillary, and a controller of a temperature of the electrophoresis capillary. The temperature sensor provides temperature data of the electrophoresis capillary. The controller changes the electrical current through the electrical path responsive to the temperature data from the temperature sensor.

In one embodiment the electrical path has at least one resistance providing temperature data of the electrophoresis capillary in thermal contact with the electrical path. The apparatus further includes a controller of a temperature of the electrophoresis capillary, which changes the electrical current through the electrical path responsive to the temperature data from the resistance of the electrical path.

One embodiment further includes at least one thermal insulation member attached to the circuit board and positioned by the electrical path and the electrophoresis capillary. The thermal insulation member reduces heat transfer between a part of the circuit board attached to the electrical path and the electrophoresis capillary, and a remainder of the circuit board. An example of such a thermal insulation member is an aperture in the circuit board.

One embodiment has multiple electrical paths in thermal contact with different sections of the electrophoresis capillary. The different sections of the electrophoresis capillary are separately thermally regulated by different electrical paths. One embodiment further includes multiple temperature sensors in thermal contact with the different sections of the electrophoresis capillary, and a controller of temperatures of the different sections of the electrophoresis capillary. The temperature sensors provide temperature data of the different sections of the electrophoresis capillary. The controller changes the electrical currents through the multiple electrical paths responsive to the temperature data from the temperature sensors. In another embodiment the multiple electrical paths have resistances providing temperature data of the different sections of the electrophoresis capillary in thermal contact with the multiple electrical paths, and the apparatus further includes a controller of temperatures of the different sections of the electrophoresis capillary, which changes the electrical currents through the multiple electrical paths responsive to the temperature data from the resistances of the multiple electrical paths. In one embodiment the electrophoresis capillary is covered by a thermally insulating material.

In one embodiment the electrophoresis capillary is attached to the circuit board. In one embodiment the electrophoresis capillary is attached to the circuit board with adhesive material.

In one embodiment the electrical path runs back and forth in a thermal area of the electrically insulating circuit board. On one embodiment an electrical path is configured as two electrical nodes connected by a plurality of electrical paths. In one embodiment the thermal area has a width no less than 5 mm. In one embodiment the thermal area widens by a part of the electrophoresis capillary entering the electrically insulating circuit board.

In one embodiment the electrically insulating circuit board has an aperture through the electrically insulating circuit board. The aperture facilitates optical interaction with the electrophoresis capillary.

In one embodiment the electrical path has at least one bend. In one embodiment the electrical path overall has an S-shape.

System Apparatus

Another aspect of the technology is an apparatus, including an electrophoresis thermal assembly, at least one analyte injector, a voltage source, a laser device, and an optical detector. The electrophoresis thermal assembly includes an electrically insulating circuit board, at least one electrical path attached to the circuit board which is thermally regulated responsive to electrical current through the electrical path, and at least one electrophoresis capillary in thermal contact with the electrical path such that the electrophoresis capillary is thermally regulated responsive to electrical current through the electrical path. The analyte injector is coupled to inject at least one electrophoresis analyte into the electrophoresis capillary. The voltage source is coupled to opposite ends of the electrophoresis capillary, providing an electrophoretic voltage difference between the opposite ends of the electrophoresis capillary. The laser device is positioned to deliver a beam from the laser device to the electrophoresis capillary. The optical detector is optically coupled to receive an optical signal from the electrophoresis capillary.

Thermal Method

One aspect of the technology is a method, comprising steps of: electrophoretically moving analytes through at least one electrophoresis capillary; and thermally heating the electrophoresis capillary via thermal contact with at least one electrical path carrying electrical current through an electrically insulating circuit board.

One embodiment further comprises: generating temperature data of the electrophoresis capillary in thermal contact with the electrical path; and changing the electrical current through the electrical path, responsive to the temperature data of the electrical path.

One embodiment further comprises: generating, via at least one temperature sensor of the electrophoresis capillary, temperature data of the electrophoresis capillary in thermal contact with the electrical path; and changing the electrical current through the electrical path responsive to the temperature data from the temperature sensor.

One embodiment further comprises: generating, via at least one resistance of the electrophoresis capillary, temperature data of the electrophoresis capillary in thermal contact with the electrical path; and changing the electrical current through the electrical path responsive to the temperature data from the resistance.

One embodiment further comprises: reducing heat transfer between a part of the circuit board attached to the electrical path and the electrophoresis capillary, and a remainder of the circuit board.

One embodiment further comprises: reducing heat transfer with at least one aperture between a part of the circuit board attached to the electrical path and the electrophoresis capillary, and a remainder of the circuit board.

In one embodiment, thermally heating includes: separately thermally heating different sections of the electrophoresis capillary via thermal contact with multiple electrical paths carrying electrical currents through the electrically insulating circuit board.

One embodiment further comprises: generating temperature data of the different sections of the electrophoresis capillary; and changing the electrical currents through the multiple electrical paths, responsive to the temperature data from the different sections of the electrophoresis capillary.

One embodiment further comprises: generating temperature data of the different sections of the electrophoresis capillary, via different temperature sensors of the different sections of the electrophoresis capillary; and changing the electrical currents through the multiple electrical paths, responsive to the temperature data from the different sections of the electrophoresis capillary.

One embodiment further comprises: generating temperature data of the different sections of the electrophoresis capillary, via resistances of the multiple electrical paths; and changing the electrical currents through the multiple electrical paths, responsive to the temperature data from the different sections of the electrophoresis capillary.

One embodiment further comprises: injecting at least one analyte into said at least one electrophoresis capillary.

One embodiment further comprises: optically exciting at least one analyte in the electrophoresis capillary; and detecting an optical signal from the excited analyte.

Optical Apparatus

Another aspect of the technology is an apparatus with multiple electrophoresis capillaries, a laser device, an optical detector, and an optical selector. The laser device is positioned to deliver a beam from the laser device to at least one electrophoresis capillary. The optical detector is optically coupled to receive an optical signal from at least one electrophoresis capillary. The laser device, optical detector, and optical selector are in an arrangement that allows the optical detector to selectively detect an optical signal from any one or more of the multiple electrophoresis capillaries.

In one embodiment, the capillaries are arranged as an array. In one embodiment, the optical selector is optically positioned between the laser device and the multiple electrophoresis capillaries. The beam from the laser device is delivered to a single electrophoresis capillary and not delivered to other electrophoresis capillaries. In one embodiment, the optical selector is a scanning objective directing the beam from the laser device to the single electrophoresis capillary and not to other electrophoresis capillaries. In one embodiment, the scanning objective is adapted to make a traversing motion relative to the beam from the laser device entering the scanning objective. In another embodiment, the optical selector is an aperture passing the beam from the laser device to the single electrophoresis capillary and not to other electrophoresis capillaries. One embodiment further includes a capillary alignment detector optically coupled to receive a reflection of the beam from the single electrophoresis capillary. The reflection indicates an alignment of the beam with the single electrophoresis capillary.

In one embodiment, the optical selector is optically positioned between the multiple electrophoresis capillaries and the optical detector. The optical signal from the multiple electrophoresis capillaries to the optical detector is limited to a single electrophoresis capillary.

Various embodiments further include a wavelength dependent beam combiner optically coupled between the laser device and the optical detector, or a spatial beam combiner optically coupled between the laser device and the optical detector.

Optical Method

Another aspect of the technology is a method, comprising the steps of: electrophoretically moving analytes through multiple electrophoresis capillaries; optically exciting at least one analyte in a first electrophoresis capillary of the multiple electrophoresis capillaries; receiving, at an optical detector, an optical signal from the optically excited analyte of the first electrophoresis capillary of the multiple electrophoresis capillaries; optically exciting at least one analyte in a second electrophoresis capillary of the multiple electrophoresis capillaries; and receiving, at the optical detector, an optical signal from the optically excited at least one analyte of the second electrophoresis capillary of the multiple electrophoresis capillaries.

In one embodiment, optically exciting includes: optically exciting at least one analyte in a single electrophoresis capillary.

In one embodiment, optically exciting includes: traversing a laser beam across the multiple electrophoresis capillaries such that the single electrophoresis capillary, with optically excited analyte, changes with time.

In one embodiment, the method further includes: detecting an alignment of the laser beam with a single electrophoresis capillary, based on a reflection of the laser beam from the single electrophoresis capillary.

In one embodiment, traversing further includes: traversing an optical objective to traverse the laser beam, while keeping the beam and the optical signal within a fixed beam combiner.

In one embodiment, traversing further includes: traversing an optical objective and beam combiner to traverse the laser beam.

In one embodiment, traversing further comprising: receiving the laser beam from a laser device at a first side of an optical objective; passing the laser beam out of a second side of the optical objective towards the multiple electrophoresis capillaries; and traversing the optical objective relative to the laser beam at the first side of the optical objective, causing the laser beam at the second side of the objective to traverse across the multiple electrophoresis capillaries.

In one embodiment, optically exciting includes: optically exciting at least one analyte in multiple electrophoresis capillaries, and the method further includes: passing the optical signal from the single electrophoresis capillary to the optical detector, and blocking the optical signal from other electrophoresis capillaries.

In one embodiment, optically exciting includes: traversing an optical selector across the optical signal from the multiple electrophoresis capillaries, such that the single electrophoresis capillary which originates the passed optical signal, changes with time.

Biochemical Thermal Method

Another aspect of the technology is a method, comprising the steps: separately regulating temperature in different sections of at least one capillary via thermal contact with different electrical paths carrying electrical currents through an electrically insulating circuit board; and moving analytes through the capillary supporting a biochemical activity in the separately thermally regulated different sections of the electrophoresis capillary.

An example of such biochemical activity is a polymerase chain reaction. The different sections of the electrophoresis capillary have different temperatures for different temperature cycles of the polymerase chain reaction.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
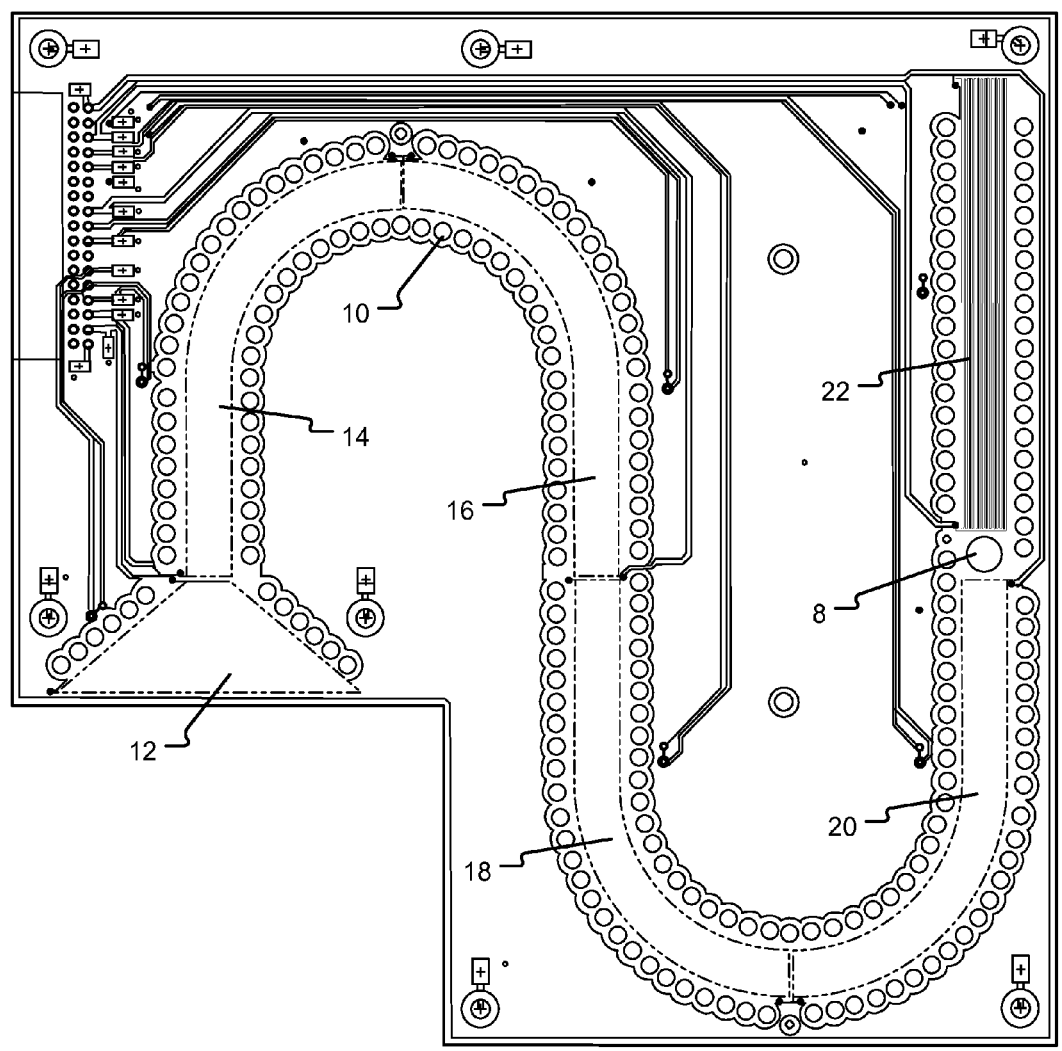
FIG. 1 is a top view of a circuit board part of a thermal assembly.

FIG. 1 is a top view of a circuit board part of a thermal assembly.

The electrically insulating circuit board has a generally S-shaped path for placement of capillaries. The generally S-shaped path is broken up into 6 different sections, 12, 14, 16, 18, 20, and 22. These 6 different sections, 12, 14, 16, 18, 20, and 22, separately regulate the temperature in the portion of a capillary in thermal contact with the particular section. Each of the different sections, 12, 14, 16, 18, 20, and 22 is filled with an electrical path that runs back and forth, e.g. in a serpentine shape in that section's area to fill that section's area. This electrical path that runs back and forth is shown in detail in section 22. Although not shown for purposes of clarity in the illustration, the other sections 12, 14, 16, 18, and 20 also are filled with an electrical path that runs back and forth in that section's area to fill that section's area.

Figure 13:
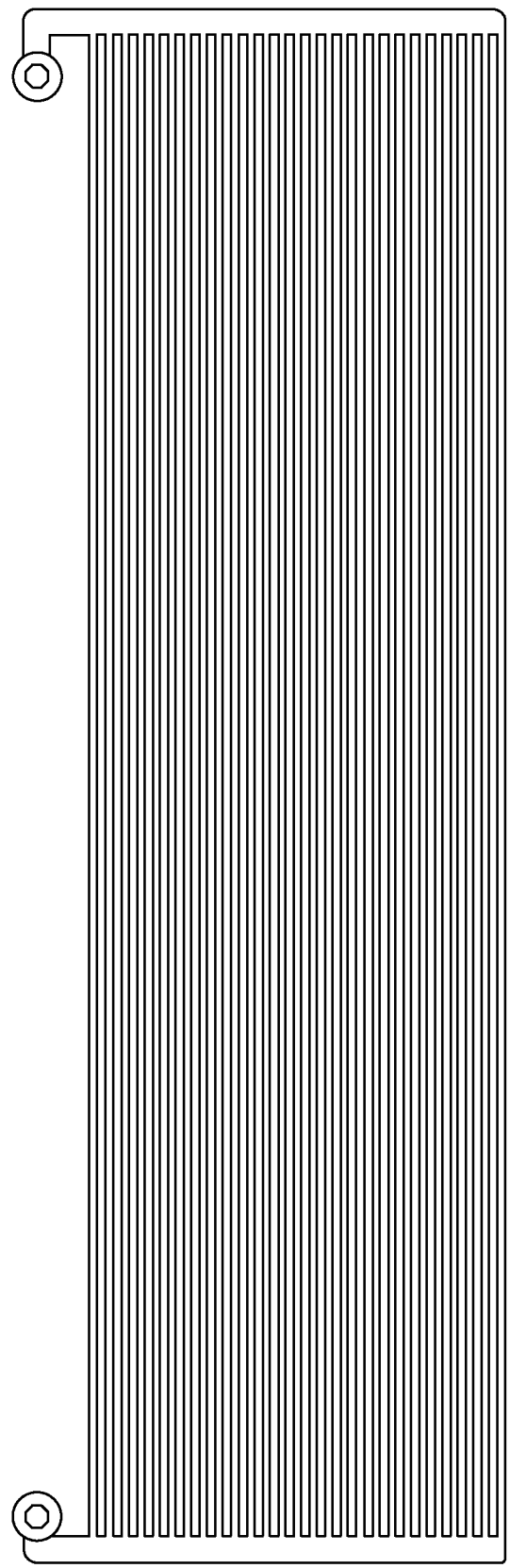
FIG. 13 shows an electrical path comprising two electrical nodes and a plurality of parallel electrical lines joining the nodes. Together, they form a thermal area.

In another embodiment, the thermal area can be formed from electrical paths configured in parallel traces joined together, for example, at common traces that attached to a voltage source or a source of current. A version of this configuration is depicted in FIG. 13.

The circuit board also has a row of apertures 10 that run along both sides of the generally S-shaped path for placement of capillaries. The apertures reduce heat transfer between the generally S-shaped path of the circuit board, and a remainder of the circuit board. Because air is a good thermal insulator, heat transfer is reduced between the two parts of the circuit board. The circuit board itself is also a poor thermal conductor. In another embodiment, instead of rows of apertures, poor thermal conductive material is positioned between these two parts of the circuit board. Such reduction of heat transfer eases thermal regulation of the generally S-shaped path and the capillaries placed on the generally S-shaped path. The apertures serve to reduce the thermal mass of the thermally regulated region to substantially the generally S-shaped path and the capillaries placed on the generally S-shaped path. With less thermal mass, a desired temperature is reached more quickly for the generally S-shaped path and the capillaries placed on the generally S-shaped path. This embodiment requires less energy. Also, the S-shaped configuration occupies less space and renders the device more easily portable.

The circuit board also includes an aperture 8 along the generally S-shaped path toward the exiting end of the generally S-shaped path. Because of the absence of circuit board material, the aperture 8 facilitates optical interaction with a capillary which is placed over the aperture 8. The aperture 8 allows for fluorescence excitation and detection using an optical configuration such as epi-fluorescent, and various skew illumination schemes.

Figure 1A:
FIG. 1A is a close-up view of an electrical path of the thermal assembly of FIG. 1.

FIG. 1A is a close-up view of an electrical path of the thermal assembly of FIG. 1.

The electrical path in various embodiments is a patterned, or etched, conductive trace bonded onto the electrically insulating circuit board. The patterned electrical path may be defined by "subtractive" patterning that removes unwanted conductive material to leave the desired conductive paths, or by "additive" patterning that adds additional conductive material to form the desired conductive paths. The circuit board may have the conductive paths on a single layer circuit board or as part of a multi-layer circuit board.

Various examples of conductive material in the electrical path are metallic material such as copper, aluminum, silver, or nonmetallic conductive material such as graphite, or conductive ink, but may be any other conductive material.

In contrast with the conductive material of the electrical path, the circuit board material is nonconductive, commonly a dielectric material.

Each electrical path creates and defines a thermal area. The current implementation has six heating areas, each comprised of approximately 1 m of 150 um wide copper traces that is folded into the shape needed to generate the heater shapes shown below. Various embodiments vary the length of the trace to shorter or longer than 1 m, depending on a length adequate for electrophoretic separation of analytes. Various embodiments widen or narrow the width of the electrical paths, depending on an adequate resistance of the electrical paths to generate adequate heat for thermal regulation of the thermally coupled capillaries. Various embodiments increase or decrease the number of heating areas.

In some embodiments, an electrical path such as a trace has a width in the range between 0.0001 to 0.5 inches, and a length in the range between 0.25 to 750 inches.

Performing electrophoresis in a capillary allows the heat to be effectively dissipated through the capillary walls. This allows high voltages to be used to achieve rapid separations.

Figure 2:
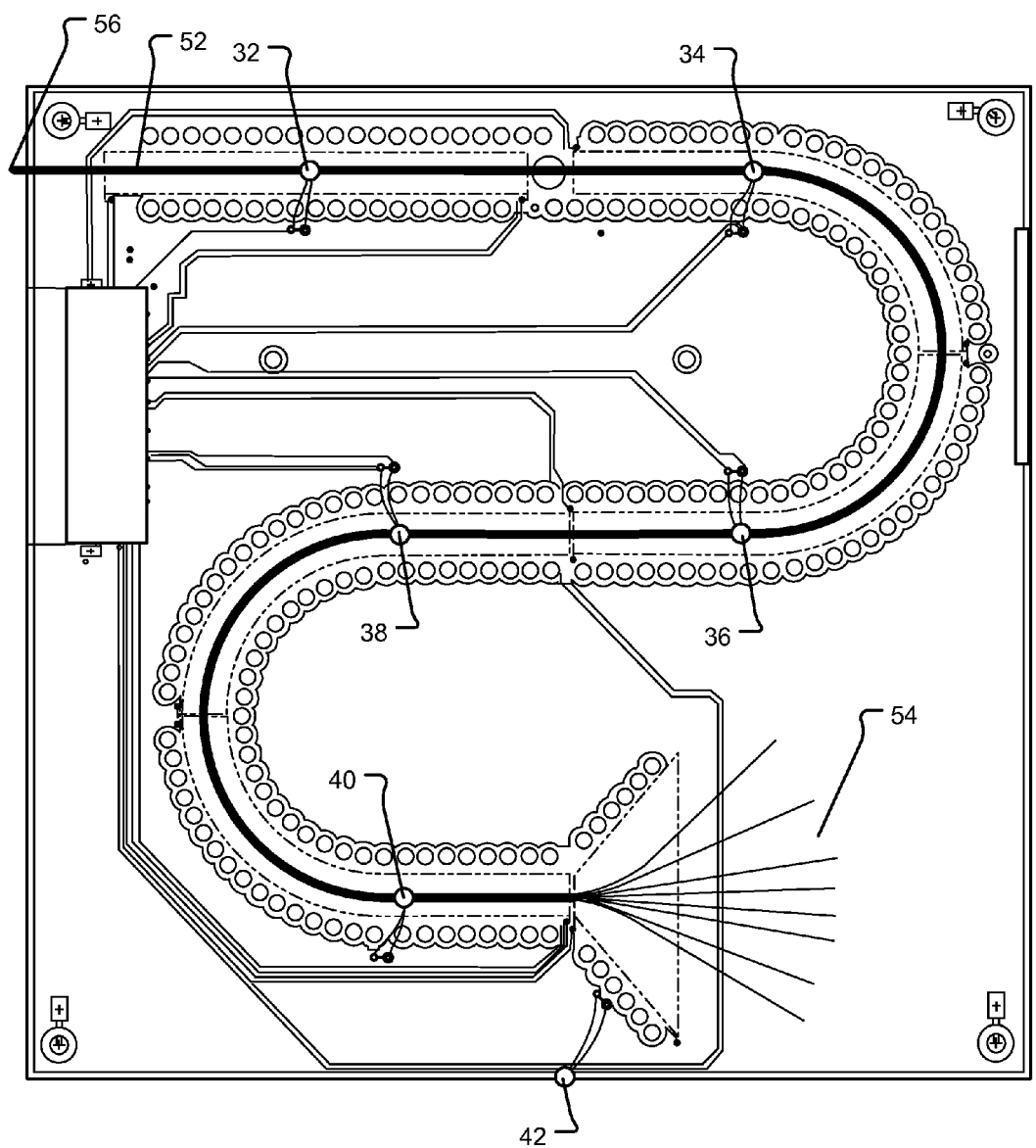
FIG. 2 is a top view of a thermal assembly, with a circuit board, electrical paths on the circuit board, a bundle of capillaries, and temperature sensors.

FIG. 2 is a top view of a thermal assembly, with a circuit board, electrical paths on the circuit board, a bundle of capillaries, and temperature sensors.

On a circuit board such as the circuit board shown in FIGS. 1 and 1A, electrophoresis capillaries are attached to the generally S-shaped path, such as by adhesive material. This shape is an optional arrangement of the capillaries. Other curves or linear arrangements also are contemplated. In the shown embodiment, a bundle of 8 capillaries are attached. Other embodiments have any other number of capillaries ranging from 1 to a higher number, depending on a particular electrophoresis application's requirements for parallel processing of analytes. The entering end 54 of the capillaries have fanned out ends, to facilitate injection of analytes into the different capillaries. The exiting end 56 of the capillaries remains bundled together in the figure.

In each of the separately thermally regulated areas or sections of the generally S-shaped path, a temperature sensor is in thermal contact. The temperature sensors shown are 32, 34, 36, 38, 40, and 42. Temperature sensor 42 is in thermal contact not with the capillaries, but the circuit board itself, or alternatively the ambient air. Examples of temperature sensors are thermistors or other temperature-varying resistance, or thermocouples or other temperature-varying voltage source. In another embodiment, the temperature data of the separately thermally regulated sections is not gathered by discrete temperature sensor, but by the electrical paths themselves such as by the resistances of the electrical paths.

In the shown embodiment, temperature sensors are thermistors that are attached to traces that terminate on a portion of the circuit board outside of the array of thermal insulation apertures. The thermistors are folded down across the capillary array and embedded in the adhesive that bonds the capillary array to the board, to ensure good thermal contact between the thermistors and the capillaries, while minimizing thermal loss from the heaters.

The temperature data generated by such temperature sensors help to thermally regulate the temperature of the capillaries in thermal contact with the electrical paths. Electrical current through the electrical path deposits thermal energy in the electrical path via Joule heating. The amount of deposited thermal energy varies with the amount of electrical current and resistance of the electrical paths.

Optical Detector

FIGS. 3, 4 11 and 12 are simplified diagrams of an optical subsystem of the electrophoresis system.

Figure 3:
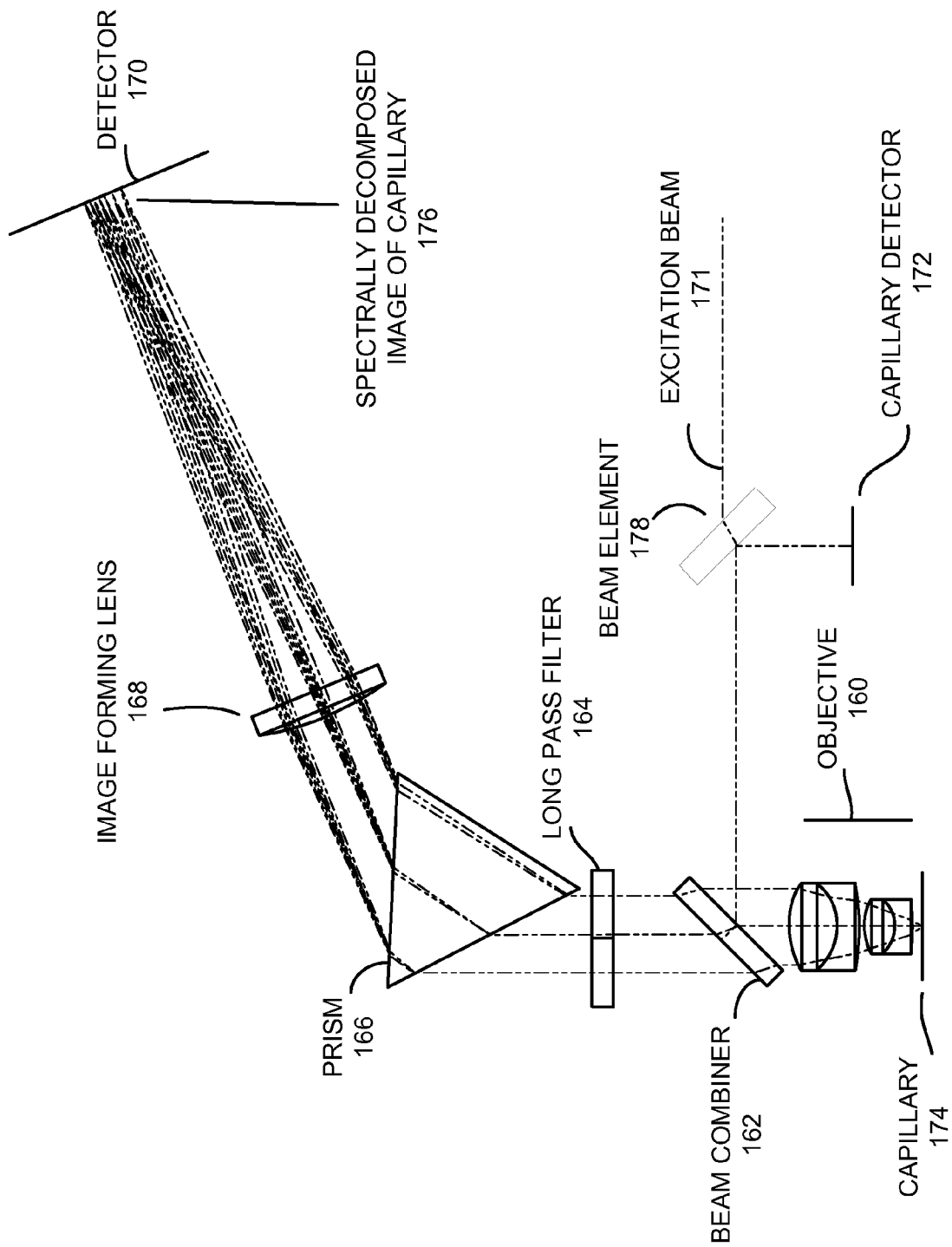
FIGS. 3 and 4 are simplified diagrams of an optical subsystem of the electrophoresis system.

In FIG. 3, the excitation source of the excitation beam 171 is a solid state laser, the output of which is projected into the capillary 174 using a beam combiner 162 placed at a 45 degree angle in the optical path immediately above the objective 160. In various embodiments the beam combiner comprises a wavelength sensitive reflector or a spatial beam splitter such as a small reflective dot placed on a transparent sheet of glass. The beam combiner is wavelength dependent, which is easier to align than a spatial beam combiner.

The high numerical aperture objective is used both by the excitation beam 171 on its way to the capillary 174, and by the optical signal of emitted fluorescence from the capillary 174.

The optical signal of fluorescence emitted from the analytes of the capillary 174 is collimated by the objective 160. The optical signal passes through the wavelength sensitive reflector 162 and impinges on a long pass filter 164 that rejects the portion of the optical signal including the excitation beam 171.

The fluorescence detection scheme is prism spectrometer based. The optical signal is then projected onto a dispersive prism 166, which serves to change the angle of the rays according to wavelength. This dispersed optical signal is then focused on the plane of the detector 170 using an image forming lens 168, causing different wavelengths of the dispersed optical signal to focus at different locations in the plane of the detector 170. An example of the detector 170 is a CCD camera. An alternative is a CMOS camera or other optical sensors.

In one embodiment, the optical subsystem described above is a point detector, to detect optical signal of analyte from a single capillary. In other embodiments, the optical subsystem further includes additional components to excite and detect the fluorescence of an array of capillaries.

In a first embodiment a shaped excitation beam illuminates the entire array of capillaries simultaneously. This creates an image in the plane of the detector which is comprised of the spectra of all the capillaries in parallel. This arrangement can result in cross talk between channels. In one embodiment, after the shaped excitation beam illuminates the entire array of capillaries simultaneously, a filter such as an aperture between the array of capillaries and the detector eliminates the optical signal from extra capillaries, thereby addressing crosstalk.

In another embodiment to capture information from all capillaries in the array, the objective is scanned across the array. In this embodiment, the objective is moved relative to a laser beam entering the objective, so that as the objective moves, the point at which the laser beam exiting the objective strikes the capillaries traverses, thereby allowing a selected capillary to be excited. In this configuration, cross talk between capillaries is eliminated because only one capillary is illuminated at a time.

With an array that comprises 200 um diameter capillaries, the scan range for the detection device covers +/−0.8 mm for an eight channel array. This limited scan range minimizes the number of moving parts. Other embodiments widen or narrow the scan range to accommodate a different number of capillaries and/or different number of capillaries. As only the objective 160 moves, the excitation laser beam 171 remains very close to the center of the objective 160, even when the beam 171 is located at the top of the end capillary in the array. The excitation beam 171 impinges on the capillaries at different angles depending on the location of the capillary in the array.

In one embodiment, the objective 160 is moved continuously, or continuously for a scan interval. With the input of the capillary detector 172 described below, the software and/or electronics of the instrument predicts that the objective will pass over a selected capillary. The detector 170 is turned on as the objective passes over a selected capillary. Alternatively, the detector 170 can remained turned on regardless of whether the objective passes over a selected capillary, and the data from the detector 170 is discarded as the detector 170 is not passing over a selected capillary, and collected or processed as the detector 170 is passing over a selected capillary.

In another embodiment, the objective 160 is moved discontinuously, such that the objective moves quickly as the objective passes over a space between capillaries, and then stops over a selected capillary sufficiently long for the detector 170 to collect optical signal from the selected capillary. This can be accomplished, for example, by using a stepper motor.

Similarly, the optical signal of fluorescent emission moves across the face of the prism 166 and the lens behind the prism 168, but the image of the spectrum remains in the same location regardless of the objective location, because the prism 166 is located in collimated optical space.

The capillary detector 172 receives a reflection of the excitation beam 171 from the capillaries by way of capillary detection beam splitter 114/beam element 178 as the scanning objective 160 passes across each capillary. The reflection varies in intensity as a function of the position of the scanning objective 160 relative to the top of each capillary. This results in a distinct intensity profile that is used by software and/or electronics embedded into the instrument that determine the locations of the capillaries, and alignment of the laser beam relative to the capillaries. That information is then used to trigger data acquisition of the optical signal striking the detector 170.

Figure 4:
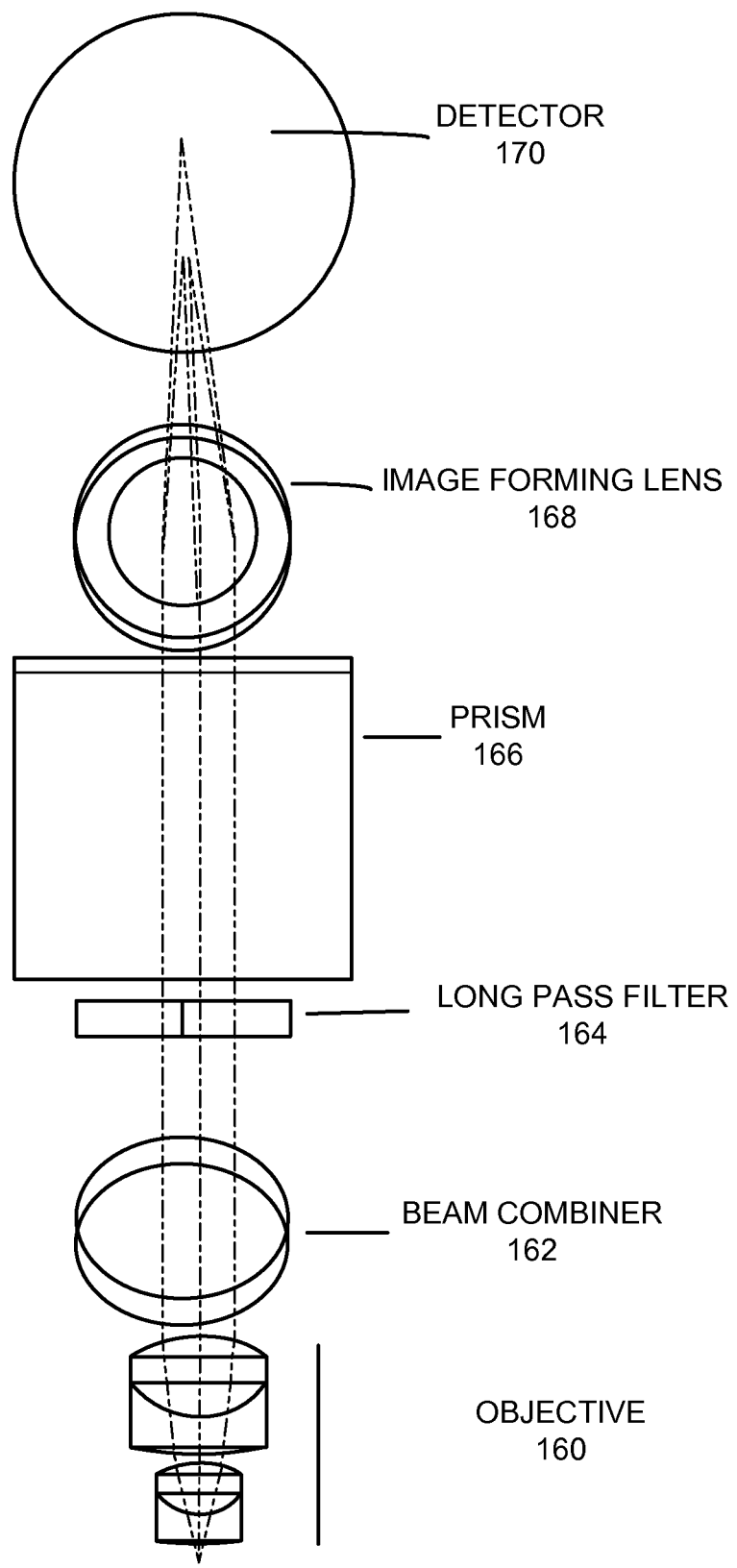

In FIG. 4, the ray trace shows the effect of the objective being off by 1 mm from mechanical center on the emission path.

FIG. 4 shows the "end view" of the optical path. FIG. 4 illustrates the effect of scanning the objective 160, on the image of the capillaries 176. Because the prism 166 is located in collimated optical space, the spectrum remains in the same location of the detector 170 regardless of the location of the objective 160.

There are various embodiments directed to alternatives of arranging the optical path around the beam combiner.

In one embodiment, a stationary beam combiner uses a dichroic mirror that reflects the excitation beam from the laser device to the capillaries, and transmits the emitted fluorescence from the analyte in the capillary to the detector. This embodiment is advantageous in that, with less mass to move, the motion mechanism is simpler. However, some embodiments with a fixed beam combiner limit the number of scannable capillaries.

In another embodiment, a beam combiner is rotated 90 degrees relative to the vertical axis in FIG. 4. In such a configuration, the beam combiner moves with the objective, similar to a CD or DVD player. Such a geometry scans larger arrays of capillaries without being limited by the boundaries of a fixed beam combiner.

In another embodiment with a beam combiner, the laser beam is transmitted and the emitted fluorescent optical signal from the sample is reflected. In such a system, the excitation and emission paths change places.

Another embodiment implements a system with a spatial beam combiner rather than a wavelength dependent beam combiner. The spatial beam combiner is implemented as a small mirror that covers a fraction of the arc of the emission path. The excitation laser is aligned to reflect off that mirror. The physical implementation of the mirror is alternatively a small reflective area on a piece of optical glass or a small physical mirror that is held in the proper location.

In another embodiment the excitation laser beam passes through a small opening in a solid mirror that reflects the majority of the emission towards the detector. Again the opening could be either a physical hole in a mirror or simply a non reflective area on a glass substrate that is otherwise coated with a mirror coating.

In various embodiments the mirror/aperture in the two cases above is located on or off of the optical axis of the system.

Figure 11:
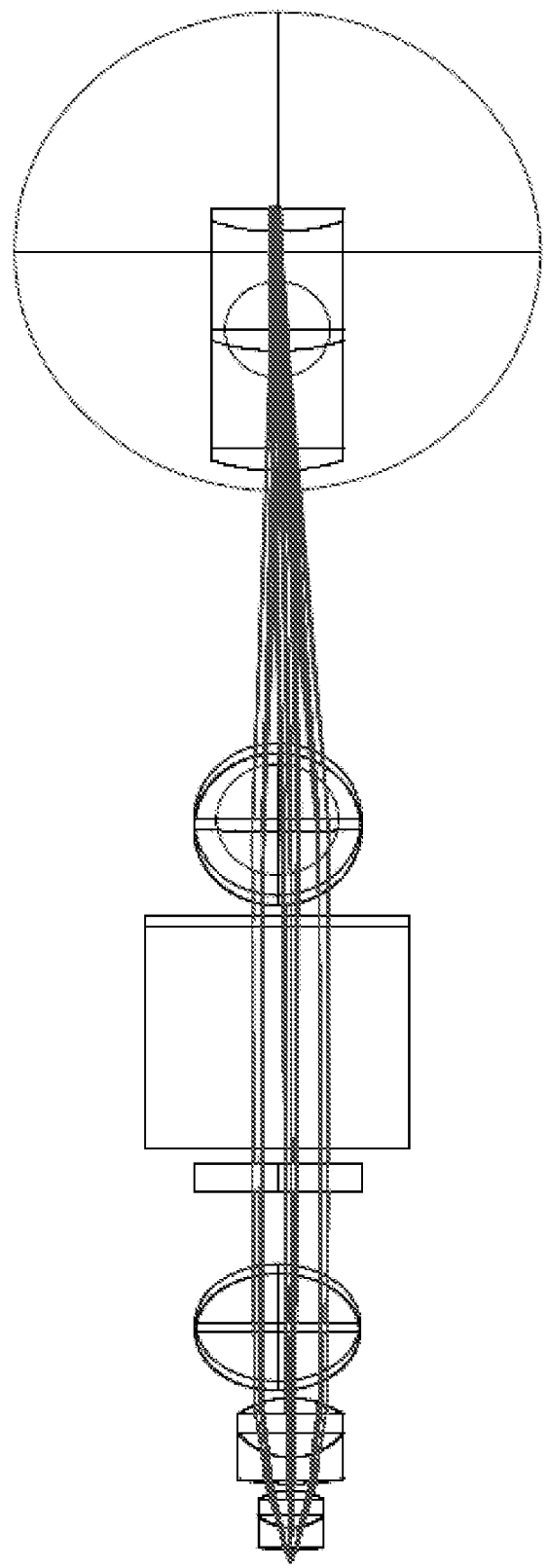
FIG. 11 shows an alternative optical subsystem of this invention comprising a cylindrical lens configured to narrow a beam of light to fall substantially along a narrow detector.
Figure 12:
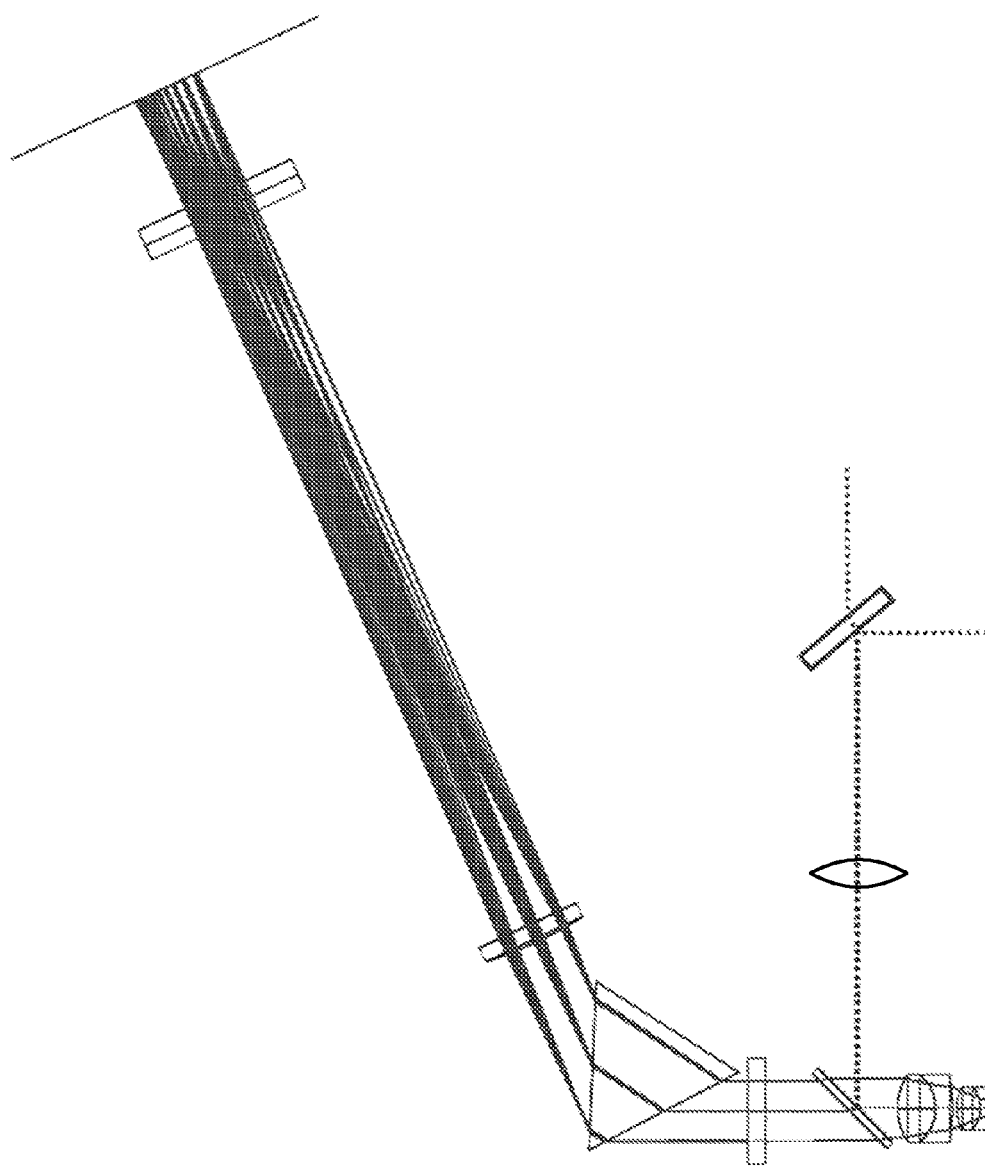
FIG. 12 shows a side perspective of the optical train of FIG. 11, also comprising a lens between two mirrors to focus light on the capillary detector.

In another embodiment, depicted in FIGS. 11 and 12, the optical path comprises a cylinder lens in the detection path to reduce alignment sensitivity of the emission path of the fluorescence detection path and allow for use of detectors with geometries that have a large length to width ratio (that are designed for line or spectrum detection purposes).

Another embodiment optionally comprises a cylindrical lens in the excitation path that produces an oblong excitation spot in the capillaries to excite a larger volume of the labeled molecules inside the capillary without affecting the spectral resolution. This improves the signal-to-noise ratio of the detected optical signal, particularly when taking into account potential photo bleaching of the dye.

FIGS. 5, 6, 7, and 8 are various perspective views of an electrophoresis system.

The layout of the electrophoresis system is generally divided into two areas: i) the laser 112 or other excitation optics 104, the capillary detection sub-system, and the actuator used to move the objective across the capillaries; and ii) the electrophoresis area 102 of the unit which includes the heaters, the capillary array, and the anode and cathode assemblies under the circuit board. The two areas are divided by a vertical wall.

Figure 5:
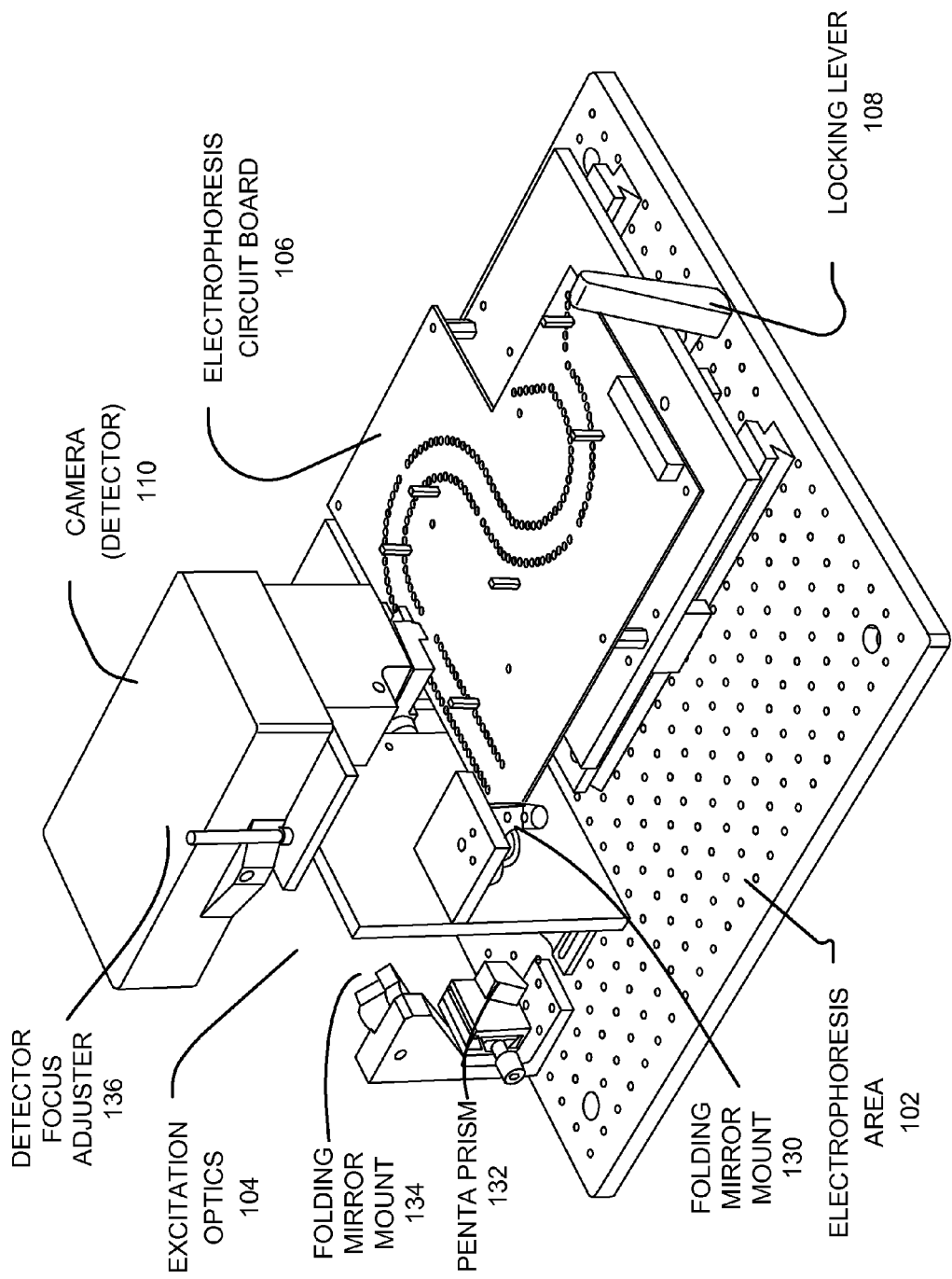
FIGS. 5, 6, 7, and 8 are various perspective views of an electrophoresis system.

In FIG. 5, a bread board implementation is shown. The detector 110 is a CCD camera. Another embodiment uses a one dimensional detector array. The figure also shows detector focus adjustor 136.

Replacement of the heater assembly can easily be accomplished by folding the locking lever 108 and pulling out the slide mounted assembly of the circuit board 106 for complete top access.

The folding mirror mount 130, 134 and the Penta prism 132 provide optical alignment of the system. The Penta prism 132 is replaced by a mirror in another embodiment.

Figure 6:
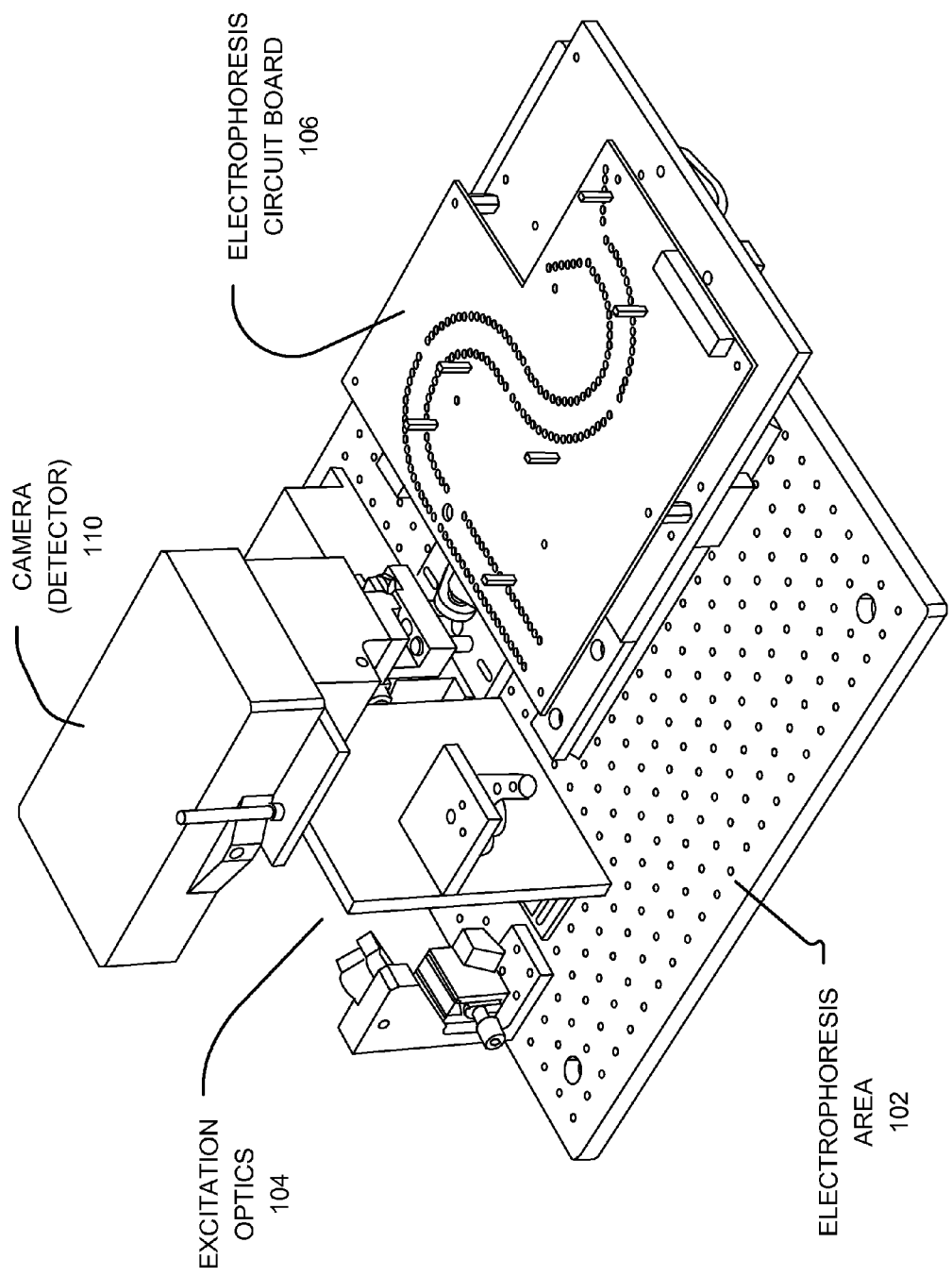

In FIG. 6, physical access to the electrophoresis circuit board is implemented.

The locking lever is in a service access position, and the capillary array assembly is in service position.

Figure 7:
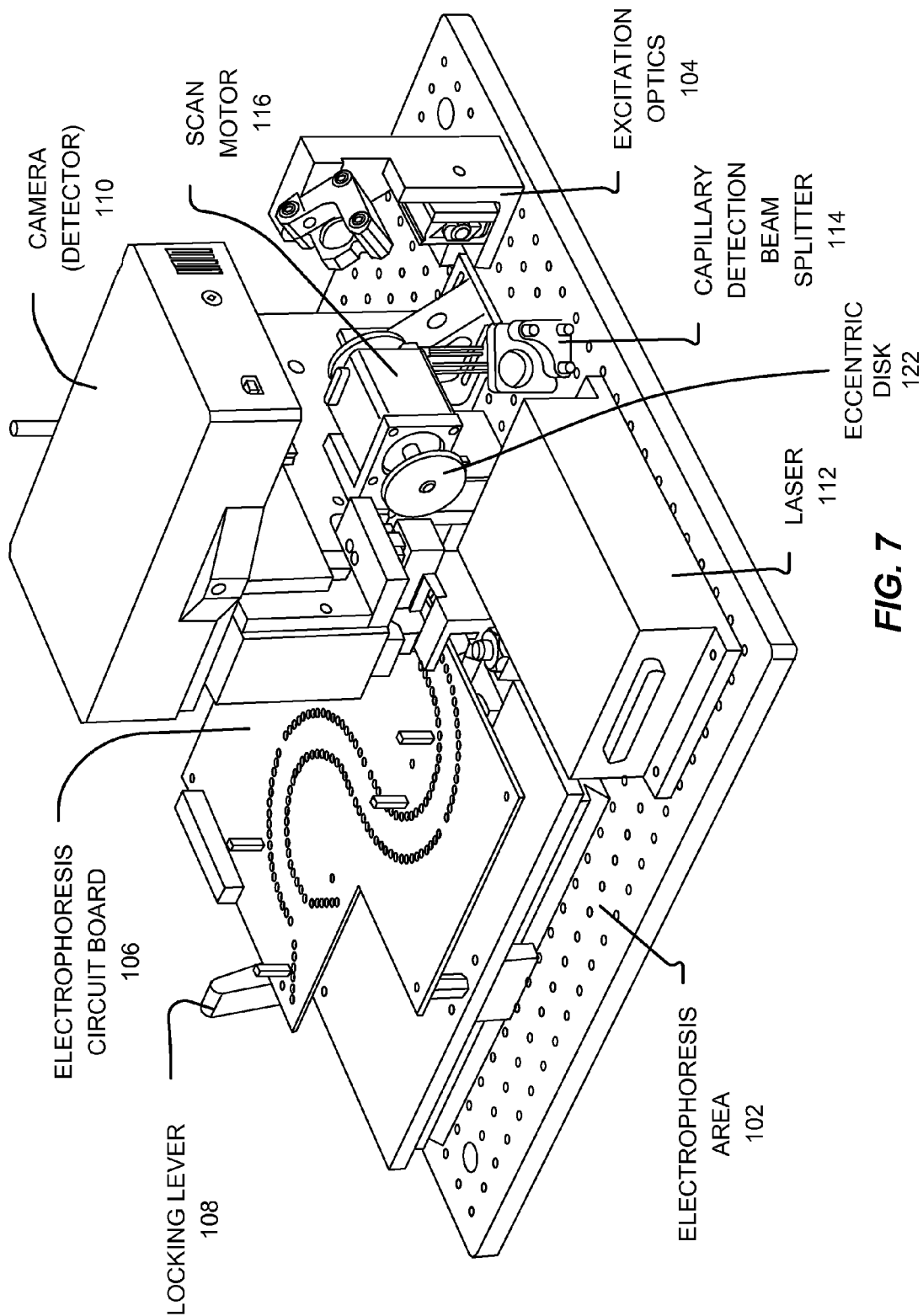

FIG. 7 shows a detailed view of the scanning mechanism of the objective.

There are many embodiments that generate accurate linear motion for the scanner. The shown embodiment is a cam driven system implemented as an eccentric disk 122, but there are many other embodiments, such as linear solenoid actuators, galvanometer mechanisms, and piezo electric actuators.

Figure 8:
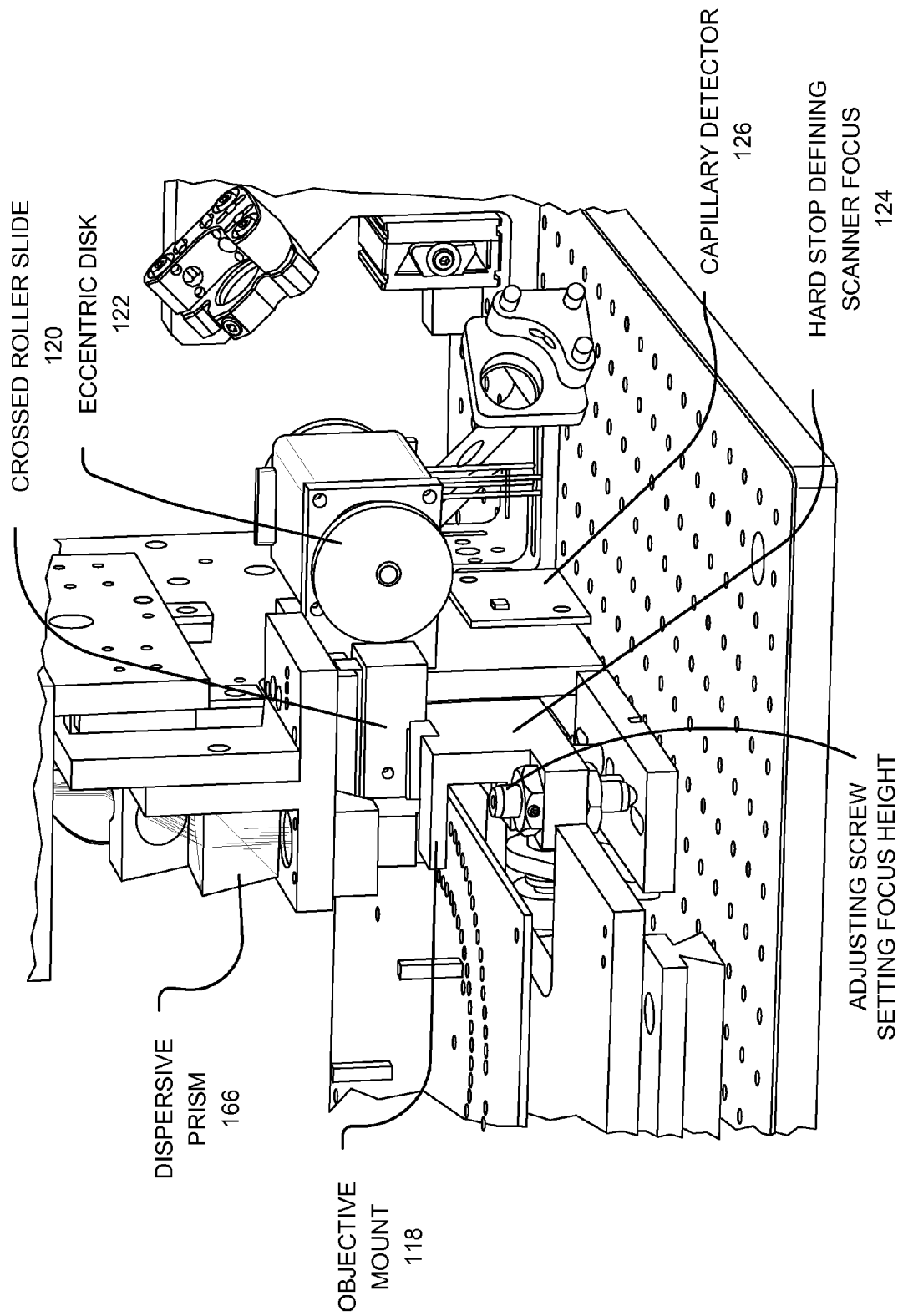

FIG. 8 shows another detailed view of the scanning mechanism of the objective.

The objective mount 118 is attached to a crossed roller slide 120 that controls its motion. A ball bearing is mounted at the end of the objective mount 118 and is held against an eccentric disk 122 by a spring (not shown). The linear back and forth motion of the objective across the capillaries is generated by rotating the eccentric disk 122 using a motor 116 (FIG. 7).

The printed circuit board heater is held against a hard stop defining scanner focus 124 which is adjusted to align the capillaries to the focal plane of the scanning optics. The focal plane is adjustable with the adjusting screw 138.

Many different embodiments of this apparatus exist. Mounting the objective to a flexure eliminates the need for the crossed roller bearing slide. A voice coil or similar actuator can also generate the linear motion.

Figure 9:
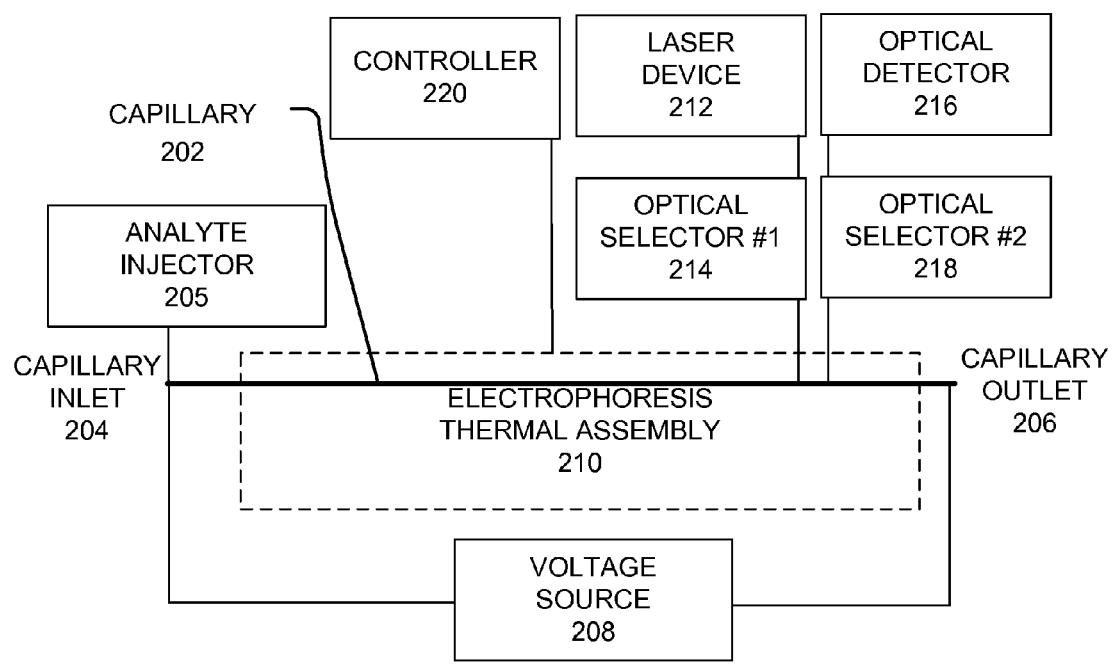
FIG. 9 is a block diagram of an electrophoresis system.

FIG. 9 is a block diagram of an electrophoresis system.

An electrophoresis thermal assembly 210, such as the one shown in FIG. 2, has one or more electrophoresis capillaries in thermal contact with electrical paths on a circuit board. A voltage source 208 facilitates the capillary electrophoresis by applying a voltage difference across the capillary inlet 204 and the capillary outlet 206 of the capillary 52. In one embodiment, the cathode of the array is located under the circuit board below the triangle shaped electrical path corresponding to the entering end of the capillaries, and the anode of the array is located under the circuit board below the exiting end of the capillaries.

An analyte injector 205 adds analyte to the capillary inlet 204. The injected analytes are electrophoretically moved through the capillary 52. Examples of injector types are gravity injection, pressure or hydrodynamic injection, and electrokinetic injection. The sample can be isolated by boluses of gas upstream and downstream to the sample. Electrophoresis buffer can also enter the capillary.

An example sample injection procedure is to dip the capillary and electrode into the sample solution vial and to apply a voltage. If the sample is ionized and the appropriate voltage polarity is used then sample ions will migrate into the capillary. This type of injection is known as electrokinetic sampling. The capillary is filled with electrolyte solution which conducts current through the inside of the capillary. The ends of the capillary are dipped into reservoirs filled with the electrolyte.

Alternative embodiments use capillary gel electrophoresis with physical gel that entangles polymers, or chemical gels with covalent structure.

In an embodiment generating temperature data from discrete temperature sensors or from the electrical paths themselves, a controller 220 raises or lowers the electrical currents to achieve a desired temperature of the capillary, or to achieve a desired temperature of a particular portion of capillary which corresponds to the electrical path in thermal contact with the particular portion of capillary. The temperature controller 220 runs current through the paths or traces on the board, causing them to heat, due to the resistance of the traces. The software running in the controller utilizes the temperature information collected by the sensors to control the temperature of the individual electrical paths using any of a variety of control algorithms to achieve a uniform temperature along the path of the capillaries. The temperature controller in one implementation is housed on a separate printed circuit board and is based on a microcontroller that controls the temperature using a PID type control algorithm to manage the temperature of each electrical path. Thermal imaging of the board in operation shows that a thermal uniformity of 2 degrees C. peak to peak is achievable over the entire length of the capillaries.

The laser device 212, optical detector 216, and one or both of optical selector #1 214 and optical selector #2 218 are arranged to limit optical signal to a single capillary. In the case of optical selector #1 214 between the laser device 212 and the capillary 202, the optical selector #1 214 limits the beam from the laser device to exciting analyte in a single capillary. In the case of optical selector #2 218 between the capillary 202 and the optical detector 216, the beam from the laser device 212 may excite analyte in one capillary or multiple capillaries, but the optical selector #2 216 limits the beam from the laser device to exciting analyte in a single capillary 202.

In various embodiments the capillary tubing has an outer diameter of about 150 to 500 microns and an inner diameter of about 10 to 100 microns. In various embodiments the capillary is polyimide or polytetrafluoroethylene clad. The capillary can be about 2 to 100 cm long, depending on the electrophoretic separation requirements.

Migration time (tm) is the time it takes to move from the beginning of the capillary to the detector window. Electrophoretic mobility, mu ($cm^2$/Vs), is the electrophoretic velocity vep (cm/s), divided by the electric field strength, E (V/cm).

Velocities are measured by dividing the migration time by the length of the capillary to the detector, Ld. Mobilities are highly dependent on the buffer type and pH as well as temperature. As the temperature increases, the viscosity decreases, and the electrophoretic mobility increases as well. Accordingly, higher temperature accelerates the electrophoresis process.

Figure 10:
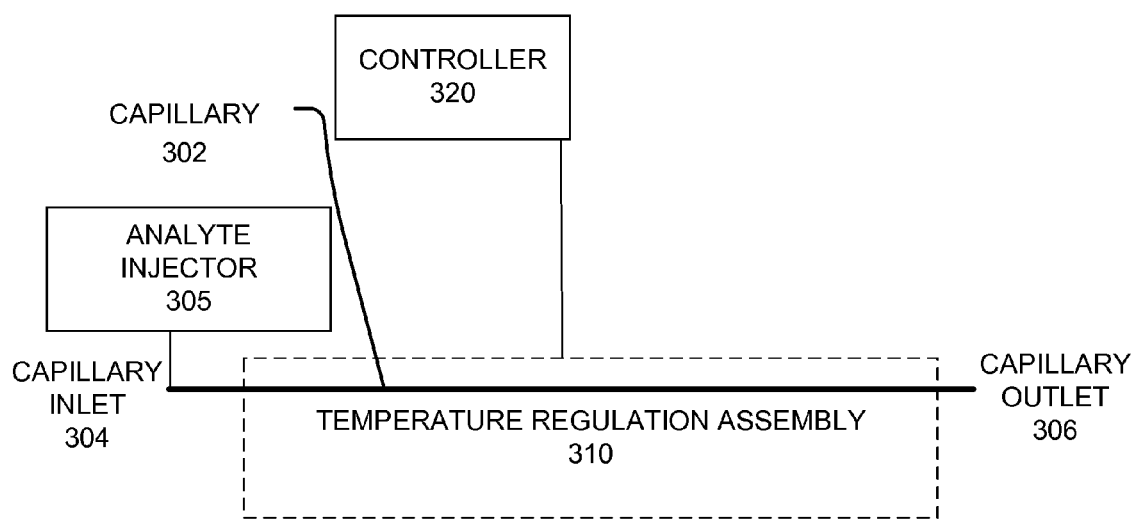
FIG. 10 is a block diagram of a temperature regulation system.

FIG. 10 is a block diagram of a temperature regulation system. One embodiment of the temperature regulation system is a thermal cycling system.

Certain biochemical reactions require appropriate temperature ranges. With a biochemical reaction performed in capillary tube, a sample is moved into a segment of the capillary at a particular temperature. Then the temperature of the sample can be changed, such as by changing the temperature of the capillary segment, or having a sequence of capillary segments and moving the sample into a subsequent segment, or some combination.

Some embodiments perform biochemical reactions requiring changes in temperature, e.g., thermal cycling reactions such as polymerase chain reaction, and subsequent product analysis (such as via the electrophoresis system of FIG. 9). This device can be used for thermal cycling of different temperatures in different electrical paths, or isothermal reactions along the different electrical paths.

A temperature regulation assembly 310, such as the one shown in FIG. 2, has one or more electrophoresis capillaries in thermal contact with electrical paths on a circuit board. A capillary 302 has a capillary inlet 304 and a capillary outlet 306.

An analyte injector 305, e.g., a DNA fragment injector, adds analyte to the capillary inlet 304.

In an embodiment generating temperature data from discrete temperature sensors or from the electrical paths themselves, a controller 320 raises or lowers the electrical currents to achieve a desired temperature of the capillary, or to achieve a desired temperature of a particular portion of capillary which corresponds to the electrical path in thermal contact with the particular portion of capillary. The temperature controller 320 runs current through the paths or traces on the board, causing them to heat, due to the resistance of the traces. The software running in the controller utilizes the temperature information collected by the sensors to control the temperature of the individual electrical paths using any of a variety of control algorithms to achieve a uniform temperature along the path of the capillaries. The temperature controller in one implementation is housed on a separate printed circuit board and is based on a microcontroller that controls the temperature using a PID type control algorithm to manage the temperature of each electrical path. Thermal imaging of the board in operation shows that a thermal uniformity of 2° C. peak to peak is achievable over the entire length of the capillaries.

PCR typically involves the following steps and temperatures: Initialization step—94-96° C. for 1-9 minutes. Denaturation step—94-98° C. for 20-30 seconds Annealing step—50-65° C. for 20-40 seconds. Extension/elongation step—around 72° C. Final elongation—70-74° C. for 5-15 minutes. Final hold—4-15° C. for an indefinite time.

These steps can be repeated as needed to perform sufficient amplification.

The capillary contains a reaction mixture and an analyte, e.g., a nucleic acid enriched from a sample (collectively referred to as the PCR reaction sample). An optical assembly can be used to monitor or control the reaction. The optical assembly can introduce or detect light. For example, an optical assembly can be used for performing real-time PCR or other real-time or end point measurements.

In one embodiment a sample preparation device can be used in conjunction with a temperature modulator as a flow-through thermal cycler. Driving force for moving the fluid can be an external pressure source or an internal pressure source. A flow-through thermal cycler can be used when highly sensitive or high throughput temperature change reaction, such as PCR, is desired. There are many situations in which one might want to sample air, blood, water, saliva, a cellular sample, or other medium in a sensitive PCR assay. This can be used to look for a variety of biological contaminants including influenza, bacterial pathogens, and any number of viral or bacterial pathogens. Flow-through PCR can allow PCR to be practiced in an automated manner without the need for human interaction. A flow-through PCR system can also serve as an early warning system in HVAC systems of buildings, airplanes, busses, and other vehicles, and can be used in the monitoring of blood, water, or other sample sources for the presence of an infectious agent or a contaminant.

The flow-through PCR device takes a sample from a collection device, such as a buccal swab, a syringe, an air sampler, fluid sampler or other sampler and delivers it to a sample preparation device. The sample is prepared in the preparation device, which in some embodiments may include cell lysis, DNA, RNA, or micro RNA enrichment or purification, filtration, or reverse transcription. In one embodiment at least one nucleic acid is enriched. In another embodiment at least one enriched nucleic acid is prepared for PCR by adding the nucleic acid to PCR reagents (such as at least one DNA polymerase, RNA polymerase, dNTPs, buffer or a salt) and primers, (such as assay-specific primers or broadly applicable primer sets for multiple target pathogens). These primers may be chosen to selectively amplify at least one nucleic acid isolated from a specific pathogen (such as a mold, virus, bacteria, parasite or amoeba), gene, other desired nucleic acid, or any combination thereof. The composition comprising at least one nucleic acid enriched from a sample, PCR reagents and primers is called a PCR reaction sample. In one embodiment, the flowthrough PCR can be used as a continuous flow device while in other embodiments samples are moved into the thermal cycling region and stopped.

The PCR reaction sample then flows through a reaction channel and circuit board with the temperature controlled electrical paths. In some embodiments the reaction channel is clear or transparent. In another embodiment the reaction channel is opaque. In one embodiment the reaction channel is a cylinder. In another embodiment the reaction channel's cross section comprises one or more planes forming a shape such as a triangle, square, rectangle, pentagon, hexagon, heptagon, octagon, nonagon, decagon, or other polygon. In one embodiment the volume of PCR reaction sample is such that it takes up a small discrete length of space in the reaction channel, the rest of which is occupied by air, gas, or a non-reactive liquid, such as mineral oil. Air, gas, or a non-reactive liquid can be used to separate individual PCR reaction samples from each other.

In one embodiment a detection module measures fluorescence, luminescence, absorbance or other optical properties to detect a signal emitted from a PCR reaction sample while it is located with a temperature control region, or after it has left a temperature control region. A detection module can comprise a light source (such as a coherent light source or incoherent light source) used to excite a fluorescent dye (such as an intercalating dye, including but not limited to ethidium bromide or Syber green) in a PCR reaction sample, and the excitation light is sensed with a photodetector (such as a CCD, CMOS, PMT, or other optical detector). Detection electronics can evaluate the signal sent from the detection module.

In one embodiment, after the desired number of thermal cycles are complete, the PCR reaction sample is pumped or pushed further down the reaction channel, using pressure or vacuum, exiting the temperature controlled region. In one preferred embodiment, a downstream device is an analytical devices that can be used for performing electrophoresis, mass spectroscopy, or other analytical techniques.

Multiple reaction channels may be used in parallel to increase sample throughput. In yet another embodiment the system may alert the user when amplification has occurred (a positive result), indicating that the target sequence is present. In one embodiment a reaction channel is used for a single use only, then disposed of. In an alternative embodiment a reaction channels can be used to amplify and detect the presence or absence of PCR amplification products in multiple samples. More than one PCR reaction samples can be loaded at intervals and interspaced with a barrier bolus of gas or liquid to prevent intermixing. In one embodiment samples are spaced apart in a manner so that as one is undergoing thermal cycling another sample is in the detection region undergoing interrogation. The PCR amplification can be replaced by other nucleic acid amplification technologies which may use thermal cycling or be isothermal reactions.

In other embodiments, the device can perform isothermal reactions such as sandwich assays using affinity reagents such as antibodies or aptamers to determine if cells, proteins, toxins, or other targets are present with the detection module providing a reading of the amount of target present. In these applications, the an affinity purification may be performed such as an IMS purification and then add a secondary antibody that may have a fluorescent label attached. The sample can then move into a thermally controlled region set to optimize the reaction. A detection module can then monitor the reaction.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. An apparatus, comprising:
   an electrically insulating circuit board;
   at least one electrical path comprising at least one conductive trace attached to the circuit board, said at least one electrical path generating Joule energy responsive to electrical current through said at least one electrical path, wherein the at least one electrical path forms at least one thermal area; and at least one electrophoresis capillary in thermal contact with said at least one thermal area, such that said at least one electrophoresis capillary is thermally regulated responsive to electrical current through said at least one electrical path.

2. The apparatus of claim 1, further comprising:
at least one temperature sensor in thermal contact with said at least one electrophoresis capillary, such that said at least one temperature sensor provides temperature data of said at least one electrophoresis capillary; and
a controller of a temperature of said at least one electrophoresis capillary, the controller changing the electrical current through said at least one electrical path responsive to the temperature data from said at least one temperature sensor.

3. The apparatus of claim 1, wherein said at least one electrical path has at least one resistance providing temperature data of said at least one electrophoresis capillary in thermal contact with said at least one electrical path, and the apparatus further comprises:
a controller of a temperature of said at least one electrophoresis capillary, the controller changing the electrical current through said at least one electrical path responsive to the temperature data from said at least one resistance of said at least one electrical path.

4. The apparatus of claim 1, further comprising:
at least one thermal insulation member attached to the circuit board and positioned by said at least one electrical path and said at least one electrophoresis capillary, said at least one thermal insulation member reducing heat transfer between a part of the circuit board attached to said at least one electrical path and said at least one electrophoresis capillary and a remainder of the circuit board.

5. The apparatus of claim 1, further comprising:
at least one aperture in the circuit board attached to the circuit board and positioned by said at least one electrical path and said at least one electrophoresis capillary, said at least one aperture reducing heat transfer between a part of the circuit board attached to said at least one electrical path and said at least one electrophoresis capillary and a remainder of the circuit board.

6. The apparatus of claim 1, wherein said at least one electrical path includes a plurality of electrical paths in thermal contact with different sections of said at least one electrophoresis capillary, such that the different sections of said at least one electrophoresis capillary are separately thermally regulated by different electrical paths of the plurality of electrical paths.

7. The apparatus of claim 6, wherein the apparatus further comprises:
a plurality of temperature sensors in thermal contact with the different sections of said at least one electrophoresis capillary, such that the plurality of temperature sensors provides temperature data of the different sections of said at least one electrophoresis capillary; and
a controller of temperatures of the different sections of said at least one electrophoresis capillary, the controller changing the electrical currents through the plurality of electrical paths responsive to the temperature data from the plurality of temperature sensors.

8. The apparatus of claim 6,
wherein said plurality of electrical paths have resistances providing temperature data of the different sections of said at least one electrophoresis capillary in thermal contact with the plurality of electrical paths, and
the apparatus further comprises:
a controller of temperatures of the different sections of said at least one electrophoresis capillary, the controller changing the electrical currents through the plurality of electrical paths responsive to the temperature data from the resistances of the plurality of electrical paths.

9. The apparatus of claim 1, wherein said at least one electrophoresis capillary is attached to the circuit board.

10. The apparatus of claim 1, wherein said at least one electrophoresis capillary is attached to the circuit board with adhesive material.

11. The apparatus of claim 1, wherein said at least one electrical path includes an electrical path that runs back and forth in said at least one thermal area or an electrical path configured as two electrical nodes connected by a plurality of electrical paths.

12. The apparatus of claim 1, wherein said at least one thermal area has a width no less than 5 mm.

13. The apparatus of claim 1, wherein the thermal area widens by a part of said at least one electrophoresis capillary entering the electrically insulating circuit board.

14. The apparatus of claim 1, wherein said electrically insulating circuit board has an aperture through the electrically insulating circuit board, the aperture facilitating optical interaction with said at least one electrophoresis capillary.

15. The apparatus of claim 1, wherein said at least one electrical path has at least one bend.

16. The apparatus of claim 1, wherein said at least one electrical path overall has an S-shape.

17. An apparatus, comprising:
(a) an electrophoresis thermal assembly, including:
an electrically insulating circuit board;
at least one electrical path comprising at least one conductive trace attached to the circuit board, said at least one electrical path generating Joule energy responsive to electrical current through said at least one electrical path;
at least one electrophoresis capillary in thermal contact with said at least one electrical path, such that said at least one electrophoresis capillary is thermally regulated responsive to electrical current through said at least one electrical path;
(b) at least one analyte injector coupled to inject at least one electrophoresis analyte into said at least one electrophoresis capillary;
(c) a voltage source coupled to opposite ends of said at least one electrophoresis capillary providing an electrophoretic voltage difference between the opposite ends of said at least one electrophoresis capillary;
(d) a laser device positioned to deliver a beam from the laser device to said at least one electrophoresis capillary;
(e) an optical detector optically coupled to receive an optical signal from said at least one electrophoresis capillary.

18. A method, comprising:
providing an apparatus comprising:
an electrically insulating circuit board;
at least one electrical path comprising at least one conductive trace attached to the circuit board, said at least one electrical path generating Joule energy responsive to electrical current through said at least one electrical path, wherein the at least one electrical path forms at least one thermal area; and
at least one electrophoresis capillary in thermal contact with said at least one thermal area, such that said at least one electrophoresis capillary is thermally regulated responsive to electrical current through said at least one electrical path;

electrophoretically moving analytes through at least one electrophoresis capillary; and thermally heating said at least one electrophoresis capillary via thermal contact with said at least one thermal area with Joule energy generated by passing electrical current through said at least one electrical path attached to said electrically insulating circuit board.

19. The method of claim 18, further comprising:

generating temperature data of said at least one electrophoresis capillary in thermal contact with said at least one thermal area; and changing the electrical current through said at least one electrical path, responsive to the temperature data of said at least one electrical path.

20. The method of claim 18, further comprising:

generating, via at least one temperature sensor of said at least one electrophoresis capillary, temperature data of said at least one electrophoresis capillary in thermal contact with said at least one thermal area; and changing the electrical current through said at least one electrical path responsive to the temperature data from said at least one temperature sensor.

21. The method of claim 18, further comprising:

generating, via at least one resistance of said at least one electrophoresis capillary, temperature data of said at least one electrophoresis capillary in thermal contact with said at least one thermal area; and changing the electrical current through said at least one electrical path responsive to the temperature data from said at least one resistance.

22. The method of claim 18, further comprising:

reducing heat transfer between a part of the circuit board attached to said at least one electrical path and said at least one electrophoresis capillary, and a remainder of the circuit board.

23. The method of claim 18, further comprising:

reducing heat transfer with at least one aperture between a part of the circuit board attached to said at least one electrical path and said at least one electrophoresis capillary, and a remainder of the circuit board.

24. The method of claim 18, wherein said thermally heating includes:

separately thermally heating different sections of said at least one electrophoresis capillary via thermal contact with a plurality of electrical paths carrying electrical currents through the electrically insulating circuit board.

25. The method of claim 24, further comprising:

generating temperature data of the different sections of said at least one electrophoresis capillary; and changing the electrical currents through the plurality of electrical paths, responsive to the temperature data from the different sections of said at least one electrophoresis capillary.

26. The method of claim 24, further comprising:

generating temperature data of the different sections of said at least one electrophoresis capillary, via different temperature sensors of the different sections of said at least one electrophoresis capillary; and changing the electrical currents through the plurality of electrical paths, responsive to the temperature data from the different sections of said at least one electrophoresis capillary.

27. The method of claim 24, further comprising:

generating temperature data of the different sections of said at least one electrophoresis capillary, via resistances of the plurality of electrical paths; and changing the electrical currents through the plurality of electrical paths, responsive to the temperature data from the different sections of said at least one electrophoresis capillary.

28. The method of claim 18, further comprising:

injecting at least one analyte into said at least one electrophoresis capillary.

29. The method of claim 18, further comprising:

optically exciting at least one analyte in said at least one electrophoresis capillary; and detecting an optical signal from said excited at least one analyte.

30. A method, comprising:

separately regulating temperature in different sections of at least one capillary via thermal contact with different thermal areas formed from different electrical paths carrying electrical currents through an electrically insulating circuit board, wherein each of said different electrical paths comprise different conductive traces attached to the circuit board, said different electrical paths generating Joule energy responsive to electrical current through said different electrical paths, wherein the different electrical path forms said thermal areas; and moving analytes through said at least one capillary supporting a biochemical activity in the separately thermally regulated different sections of said at least one electrophoresis capillary.

31. The method of claim 30 wherein the biochemical activity is polymerase chain reaction or a sandwich assay using affinity reagents.

32. The method of claim 31 wherein the capillary contains at least one DNA polymerase dNTPs and primers.

33. The method of claim 30 comprising moving the analytes through thermal areas adapted for PCR including thermal areas adapted for a denaturation step; an annealing step and an extension/elongation step.

34. The method of claim 33 wherein the thermal area adapted for a denaturation step has a temperature between 94-98° C., the thermal area adapted for an annealing step has a temperature between 50-65° C.; and the thermal area adapted for extension/elongation step has a temperature around 72° C.

35. The method of claim 30 comprising moving the analytes through thermal areas adapted for PCR including a thermal area adapted for an initialization step having a temperature between 94-96° C.; a thermal area adapted for a denaturation step having a temperature between 94-98° C., a thermal area adapted for an annealing step having a temperature between 50-65° C.; a thermal area adapted for extension/elongation step has a temperature around 72° C.; a thermal area adapted for final elongation having a temperature between 70-74° C. and a thermal area adapted for final hold having a temperature between 4-15° C.

* * * * *